United States Patent [19]
Hart et al.

[11] Patent Number: 6,099,553
[45] Date of Patent: Aug. 8, 2000

[54] SUTURE CLINCH

[75] Inventors: Charles C. Hart, Huntington Beach; Nabil Hilal, Mission Viejo; Said Hilal, Laguna Niguel, all of Calif.

[73] Assignee: Applied Medical Resources Corporation, Laguna Hills, Calif.

[21] Appl. No.: 09/082,495

[22] Filed: May 21, 1998

[51] Int. Cl.[7] .............................. A61B 17/04; A44B 1/04
[52] U.S. Cl. ........................ 606/232; 606/148; 606/151; 606/157; 24/115 A; 24/265 A
[58] Field of Search .................... 606/232, 151, 606/157, 158, 120; 24/115 A, 265 A

[56] References Cited

U.S. PATENT DOCUMENTS

| | | | |
|---|---|---|---|
| 1,352,091 | 9/1920 | Shand | 24/115 A |
| 3,753,438 | 8/1973 | Wood et al. | 128/335 |
| 3,875,648 | 4/1975 | Bone | 29/417 |
| 4,006,747 | 2/1977 | Kronenthal et al. | 128/335 |
| 4,039,078 | 8/1977 | Bone | 206/343 |
| 4,235,238 | 11/1980 | Ogiu et al. | 128/334 R |
| 4,291,698 | 9/1981 | Fuchs et al. | 128/335 |
| 4,387,489 | 6/1983 | Dudek | 24/133 |
| 4,448,194 | 5/1984 | DiGiovanni et al. | 128/334 R |
| 4,589,626 | 5/1986 | Kurtz et al. | 251/10 |
| 4,627,437 | 12/1986 | Bedi et al. | 128/334 C |
| 4,669,473 | 6/1987 | Richards et al. | 128/334 C |
| 4,705,040 | 11/1987 | Mueller et al. | 128/334 R |
| 4,724,840 | 2/1988 | McVay et al. | 128/334 R |
| 4,741,330 | 5/1988 | Hayhurst | 128/92 YF |
| 4,823,794 | 4/1989 | Pierce | 128/335 |
| 4,841,888 | 6/1989 | Mills et al. | 112/169 |
| 5,021,059 | 6/1991 | Kensey et al. | 606/213 |
| 5,041,129 | 8/1991 | Hayhurst et al. | 606/232 |
| 5,078,731 | 1/1992 | Hayhurst | 606/232 |
| 5,080,663 | 1/1992 | Mills et al. | 606/144 |
| 5,085,661 | 2/1992 | Moss | 606/139 |
| 5,282,832 | 2/1994 | Toso et al. | 606/232 |
| 5,330,442 | 7/1994 | Green et al. | 606/232 |
| 5,366,461 | 11/1994 | Blasnik | 606/151 |
| 5,376,101 | 12/1994 | Green et al. | 606/232 |
| 5,441,509 | 8/1995 | Vidal et al. | 606/151 |
| 5,462,558 | 10/1995 | Kolesa et al. | 606/139 |
| 5,474,572 | 12/1995 | Hayhurst | 606/232 |
| 5,507,757 | 4/1996 | Sauer et al. | 606/144 |
| 5,514,159 | 5/1996 | Matula et al. | 606/232 |
| 5,520,702 | 5/1996 | Sauer et al. | 606/144 |
| 5,524,327 | 6/1996 | Mickel et al. | 24/115 |
| 5,626,590 | 5/1997 | Wilk | 606/148 |
| 5,626,613 | 5/1997 | Schmieding | 606/232 |
| 5,643,289 | 7/1997 | Sauer et al. | 606/139 |
| 5,669,917 | 9/1997 | Sauer et al. | 606/139 |
| 5,690,655 | 11/1997 | Hart et al. | 606/148 |
| 5,709,694 | 1/1998 | Greenberg et al. | 606/148 |
| 5,725,542 | 3/1998 | Yoon | 606/157 |
| 5,810,853 | 9/1998 | Yoon | 606/151 |

*Primary Examiner*—Gary Jackson
*Attorney, Agent, or Firm*—Richard L. Meyers

[57] ABSTRACT

A suture system for closing a wound defined by tissue portions includes an elongate suture having a pair of ends adapted for threading relative to the tissue portions leaving the suture ends free. A securing mechanism has a first position for capturing the suture ends and a second position for permanently holding the suture ends in a fixed relationship, with the suture tensioned to maintain the tissue portions in close proximity. In a third position, the securing mechanism frictionally engages the suture ends in a sliding relationship. In an associated method, continuous tension is placed on the suture ends during operation of the securing mechanism.

27 Claims, 19 Drawing Sheets

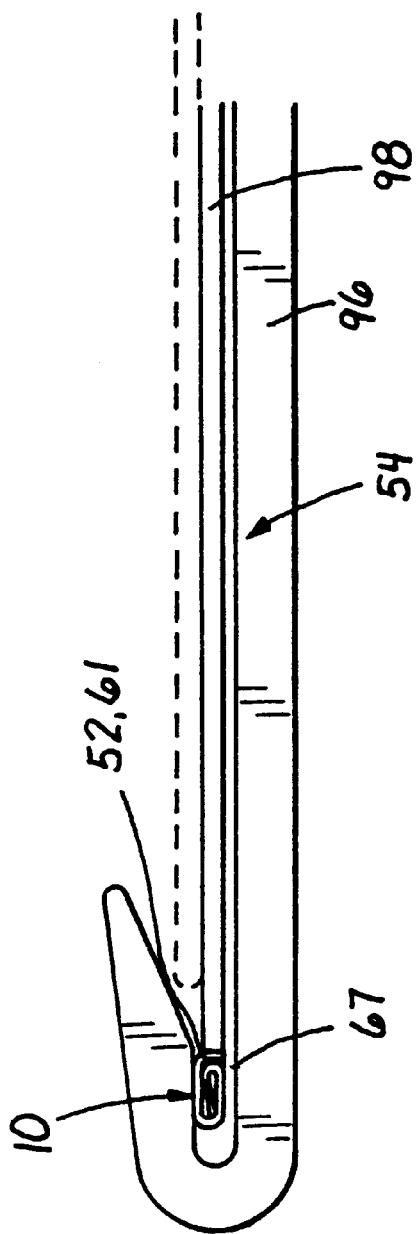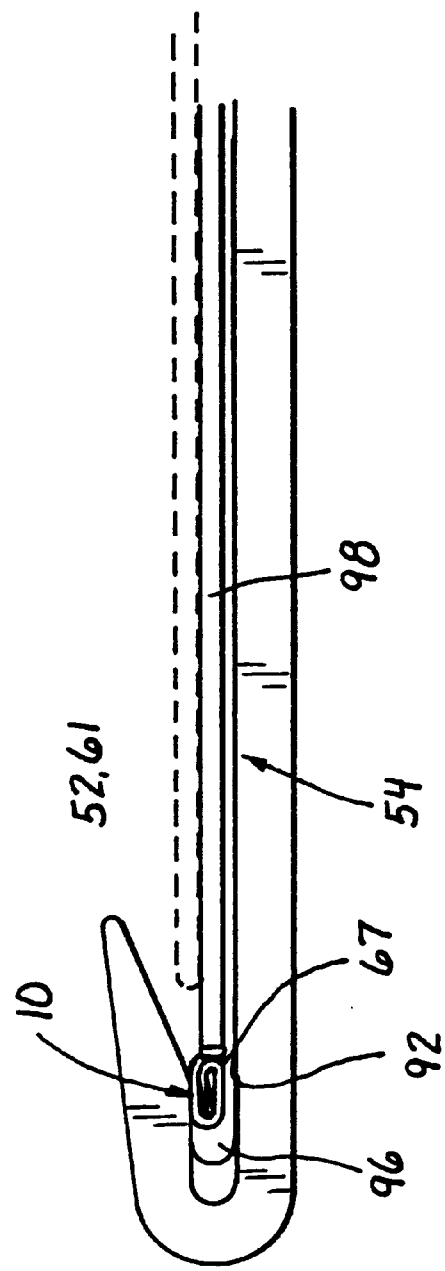

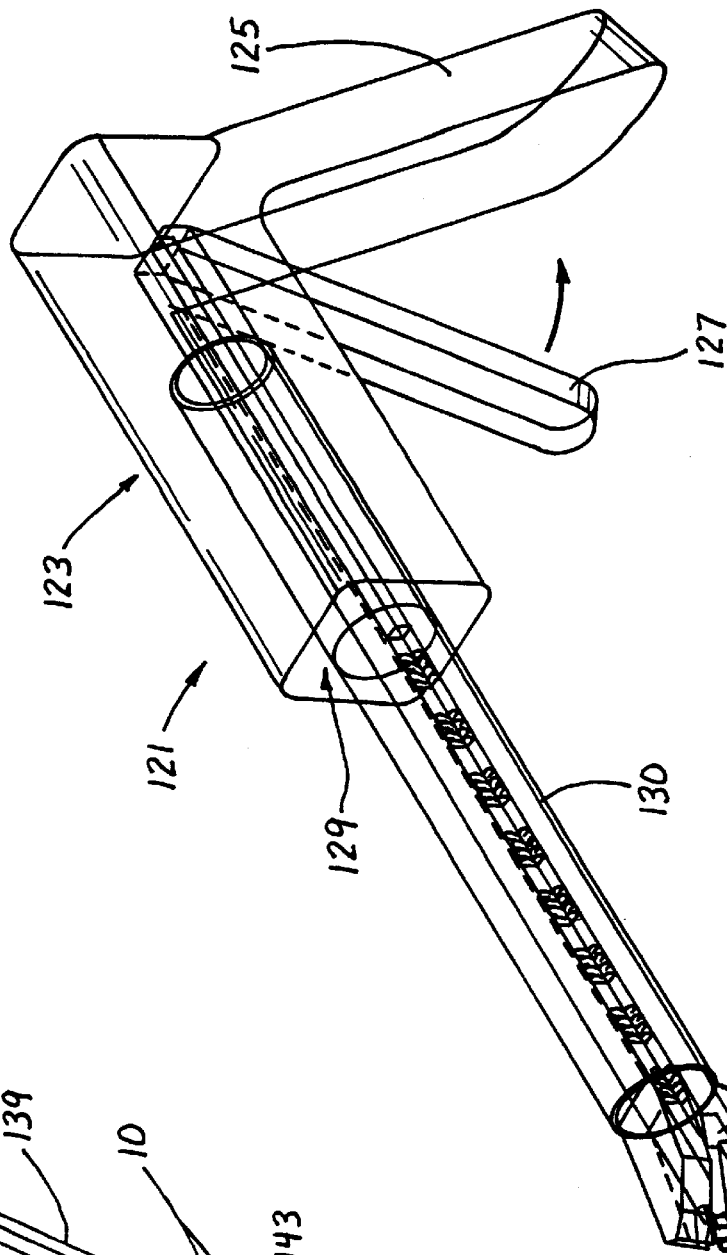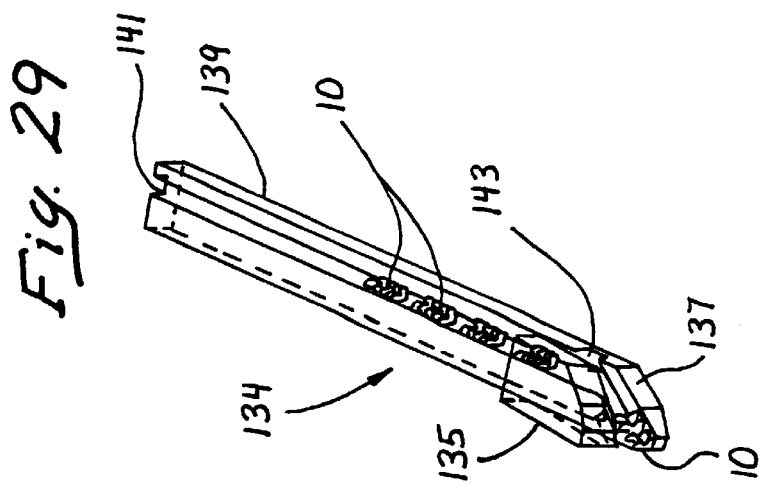

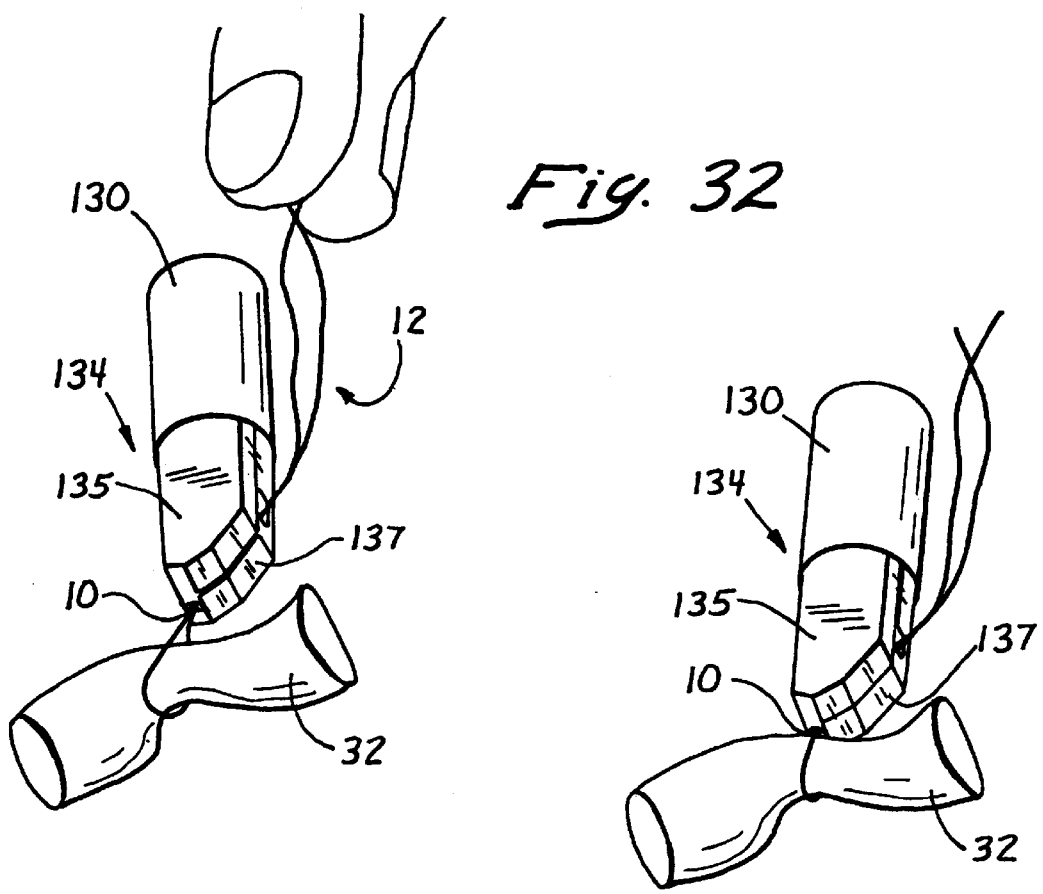
Fig. 32
Fig. 33
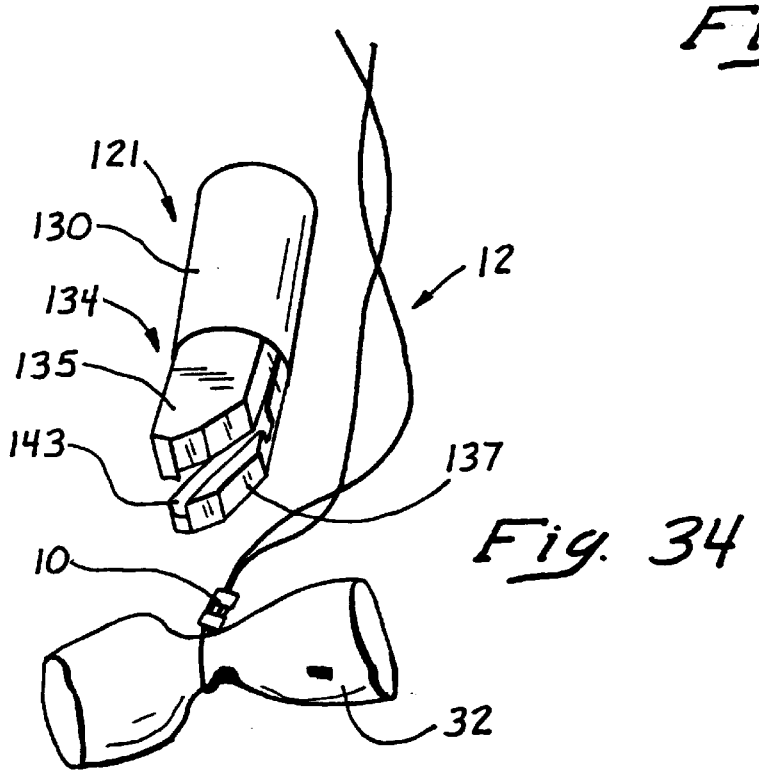
Fig. 34

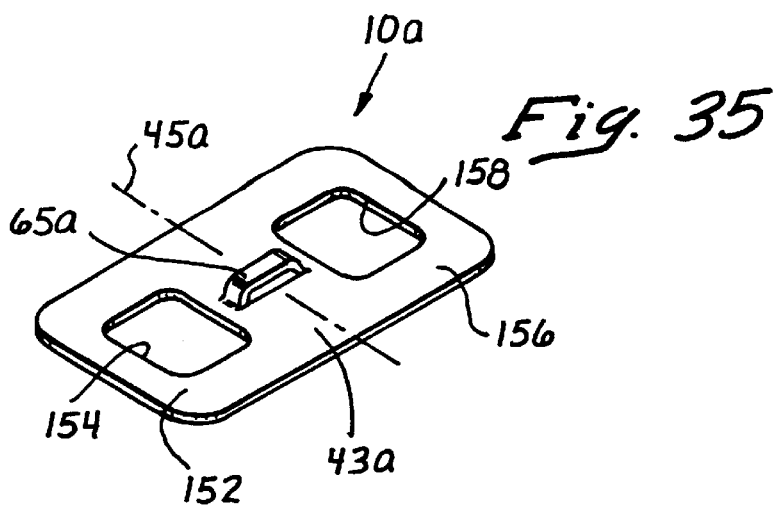
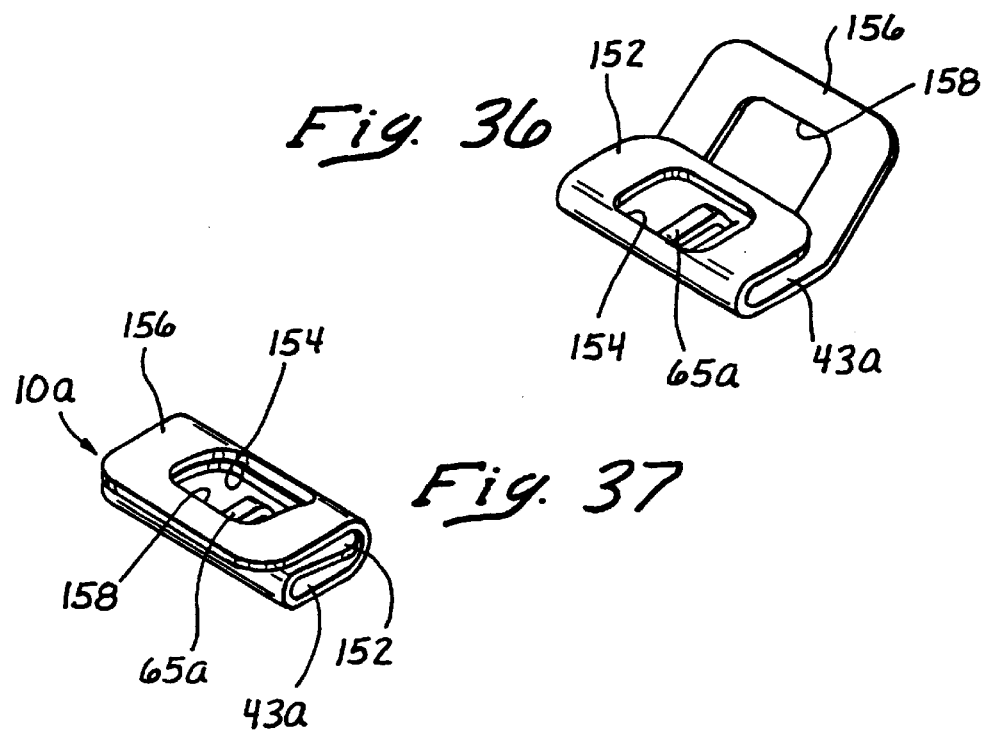
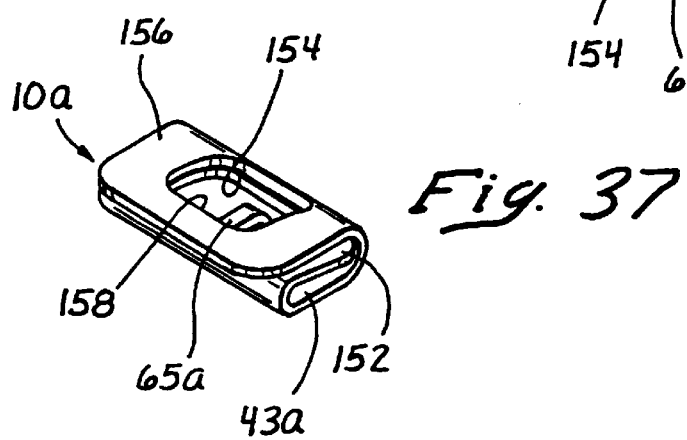
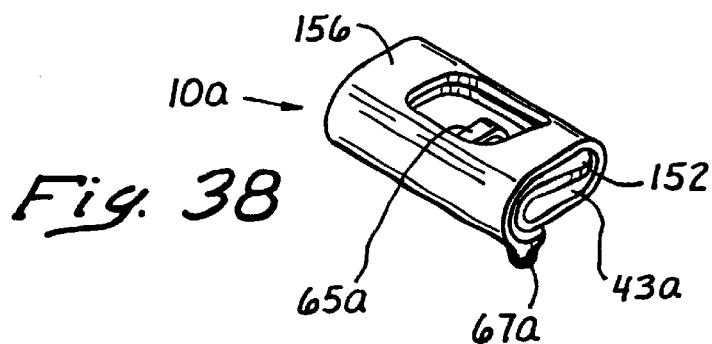

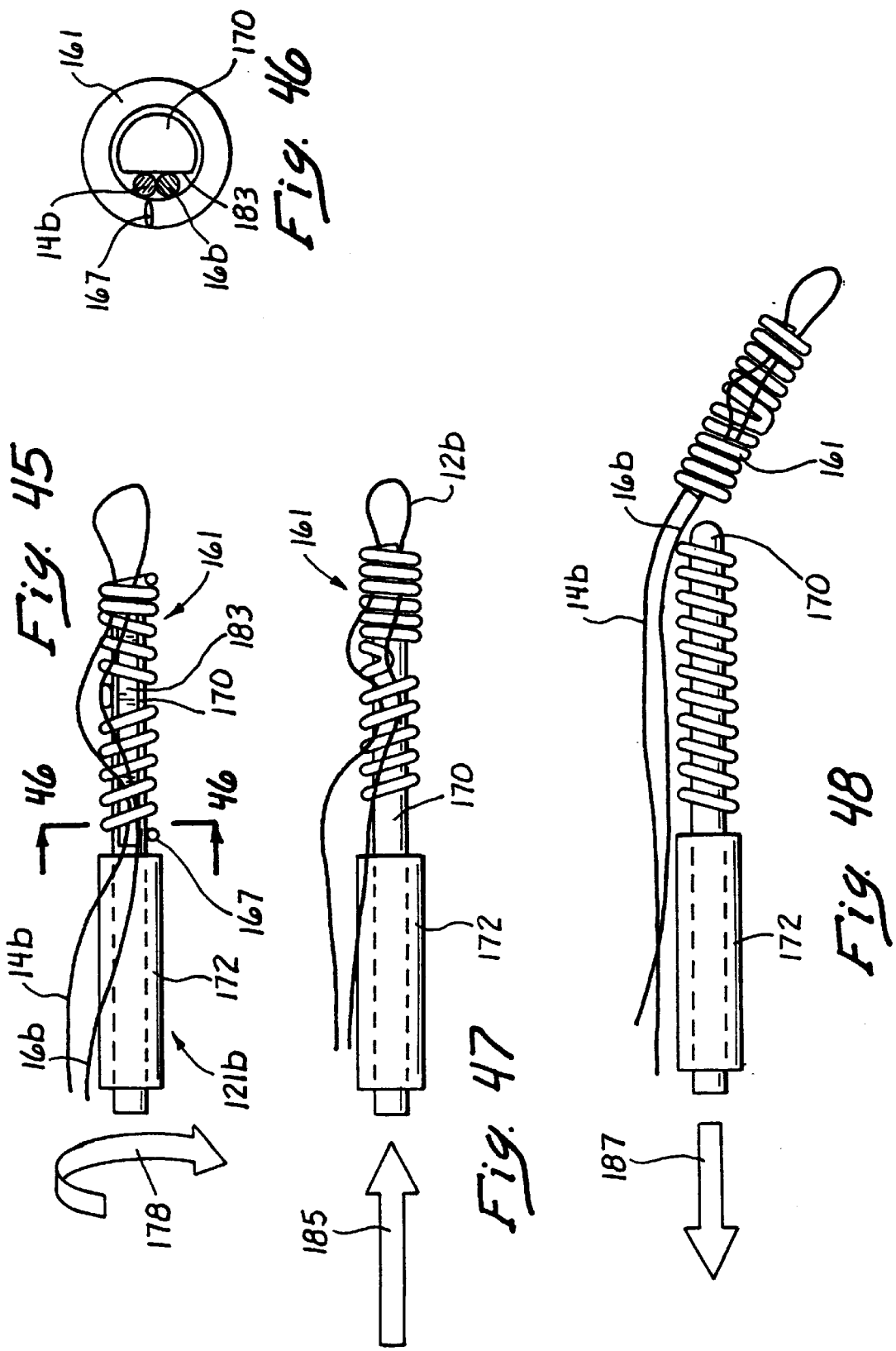

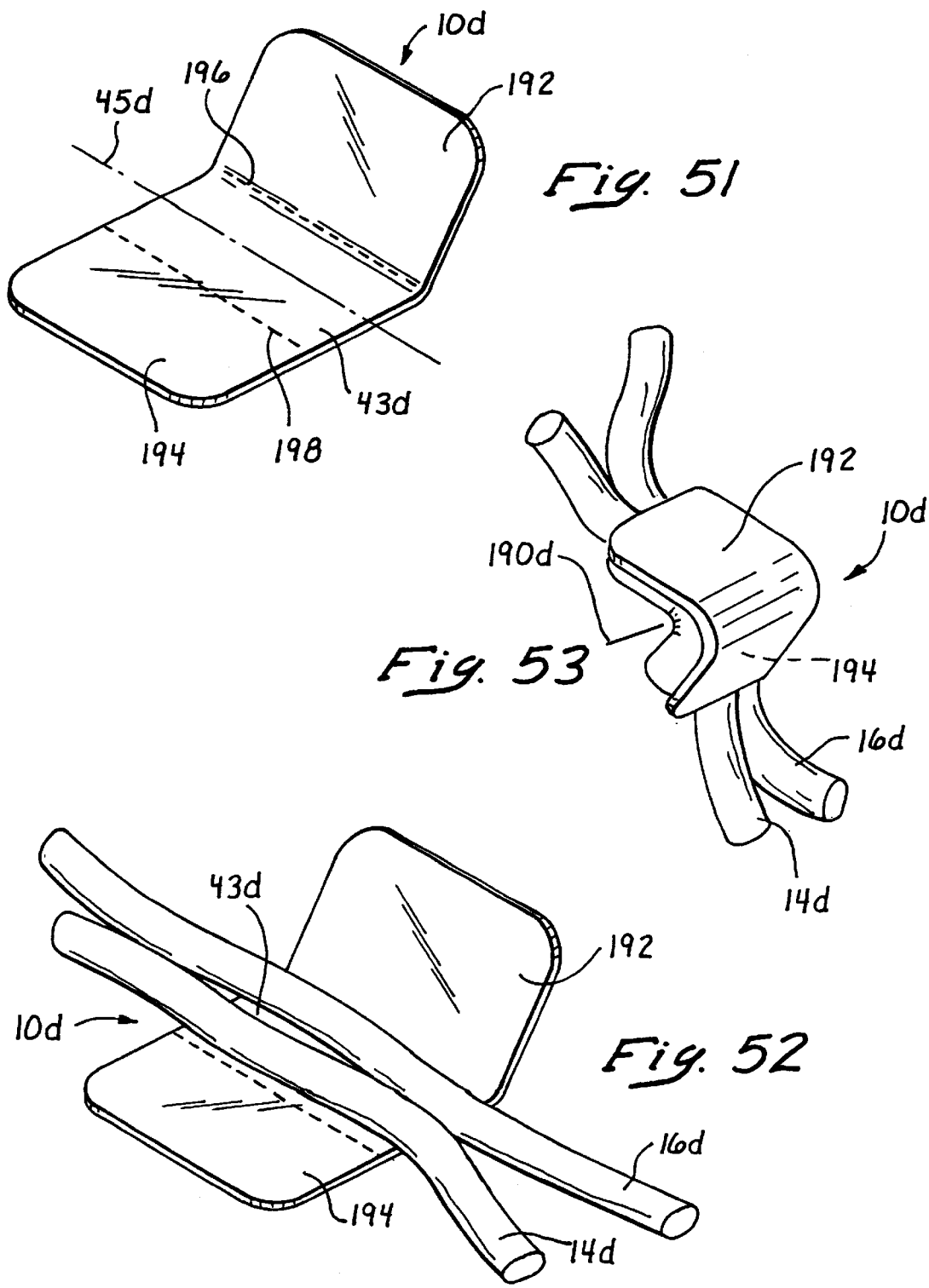

SUTURE CLINCH

BACKGROUND OF THE INVENTION

1. Field of the Invention

This invention relates generally to apparatus and methods for engaging and holding tissue, and more specifically to such apparatus and methods involving use of a suture.

2. Discussion of the Prior Art

When a wound is created in body tissue, either intentionally in the case of an incision, or unintentionally in case of an accident, it is desirable to close the site by engaging tissue portions on either side of the separation and drawing those portions into close proximity. Over time, tissues in close proximity will form a scar closing the wound.

Wound-closure systems of the past have included adhesives and clamps. However, the most common closure devices typically involve sutures which can be threaded through the opposing tissue portions and pulled tight to close the wound. In order to hold the suture taught over an extended period of time, a knot is commonly formed in the suture ends. Most surgeons would agree that suturing is an art form learned over an extended period of time. There are many types of sutures and knots, each providing certain advantages in a particular operative setting. At least as complicated as the suturing itself is the knot-tying which must occur to secure each of the sutures. Where individual sutures are placed to close a long wound, an individual knot must be tied in each place.

Knots differ considerably in their configuration, function, complexity, and characteristics. By way of example, it will be noted that knots typically involve several throws of the suture ends relative to each other. In one common knot, three half-hitches are used with the first half-hitch having four throws and each subsequent half-hitch having three throws. In this case, the tying of a single knot to close a single suture involves ten throws. The simpler knots may be easier to tie, but in distant locations even the simple knots can be complicated where it is difficult to achieve proximity to the suture site. In these locations, more complicated slip knots have been used. These knots can be tied at a remote location and then slipped down to the surgical site. Except for a few extremely complex knots, such as the Tayside knot or Roeder, slip knots have the undesirable tendency to slip in both directions. As a result, their ease of tying and movement to the surgical site is offset by their tendency to lose their grip at the suture site.

From these few examples it can be appreciated that knots, as a suture-closing system, are time-consuming, difficult to tie, hard to place, often unreliable as a holding system, difficult to adjust and impossible to relocate. Especially in the context of a laparoscopic procedure, it is noteworthy that the surgeon may lose the tactile feedback associated with tension on the suture as the knot is being tied due to the remote nature of the laparoscopic modality.

SUMMARY OF THE INVENTION

The present invention includes a suturing system which overcomes the disadvantages associated with suture knots, clamps, and adhesive. The system involves a suture but further comprises a mechanical securing mechanism which is operable at a remote location to engage the suture ends, is slidable along the suture ends for adjustable placement at a preferred position, and then is closable at that position to hold the suture ends in non-slip proximity while maintaining the desired tension on the suture. Importantly, this entire procedure can be accomplished with the surgeon holding and maintaining a known and appropriate tension on the suture ends. At no time prior to final closure of the mechanism does the surgeon lose this tactile feedback or his control of the suture. The securing mechanism can be mounted on and operated by an applier to even further facilitate its use, for example, in remote locations.

In one aspect of the invention, a suture system is adapted for closing a wound defined by tissue portions. The suture system includes an elongate suture having a pair of ends which is adapted for threading through the tissue portions leaving the suture ends free. A securing mechanism is included in the system and has a first position for capturing the suture ends and a second position for permanently holding the suture ends in a fixed relationship with the suture tensioned to maintain the tissue portions in close proximity. The securing mechanism has a third position for frictionally engaging the suture ends to hold the suture ends while permitting sliding of the securing mechanism along the suture ends. A plurality of tines are included in the securing mechanism, each having an open state and a closed state. At least one of the tines is in the closed state when the securing mechanism is in the third position. This system is operable by only one hand of the surgeon leaving the other hand available to receive tactile feedback from tension on the suture.

In another aspect of the invention, the securing mechanism includes a support extending along an axis with a first set of tines coupled to the support on one side of the axis and a second set of tines coupled to the support on the other side of the axis. Each of the tines has a first state wherein the securing mechanism is adapted to receive the suture ends and a second state wherein the securing mechanism is adapted to maintain the suture ends in a fixed relationship. At least one of the first set of tines is folded over the support in the first state.

A further aspect of the invention involves a method for fixing a tensioned suture having a pair of free ends. The method includes the step of providing a suture mechanism having a first position wherein the mechanism is adapted to receive the suture ends and a second position wherein the mechanism is adapted to hold the suture ends in a fixed relationship. The free ends of the suture are received in the mechanism in the first position. Moving the securing mechanism to the second position causes the suture ends to follow a torturous path in order to maintain the securing mechanism in a fixed position along the suture ends and to maintain the suture ends in a fixed relationship with the securing mechanism. Continuous tension is maintained on the suture ends both when the free ends received in the securing mechanism and when the securing mechanism is moved to the second position. The securing mechanism is and can be provided with a third position wherein the suture ends are captured in slidable engagement by the mechanism. This permits the securing mechanism to be moved along the suture ends to a final position and adjusted at the final position prior to fixing the mechanism on the suture ends.

DESCRIPTION OF THE DRAWINGS

FIG. 11 is a perspective view of the clinch in the open state;

FIG. 12 is a perspective view showing suture ends disposed within the clinch in the open state;

FIG. 13 illustrates the clinch with a first tine partially closed to capture the suture ends;

FIG. 14 is a perspective view of the clinch with the first tine fully closed to capture the suture ends;

FIG. 15 is a perspective view showing a second tine partially closed;

FIG. 16 is a perspective view of the clinch showing the second tine fully closed on the suture ends;

FIG. 17 is a perspective view of the suture clinch showing a third tine opposing the second tine and partially folded over the second tine;

FIG. 18 is a perspective view of the clinch with a fourth tine opposing the first tine and fully closed over the first tine;

FIG. 19 is a perspective view of the clinch with the third tine fully closed over the second tine;

FIG. 20–FIG. 27 illustrate progressive views of the suture clinch being disposed for operation within an embodiment of the clinch applier;

FIG. 20 is a top view of the clinch and applier;

FIG. 21 is a side elevation view showing the clinch in the open state and movable by a carriage of the applier;

FIG. 22 is a side elevation view illustrating movement of the carriage to partially close the first and second tines of the clinch;

FIG. 23 is a side elevation view similar to FIG. 22 and illustrating operation of the actuator to close the third and fourth tines of the clinch;

FIG. 24 is a side elevation view illustrating distal movement of the carriage to partially close the first and second tines of the clinch;

FIG. 25 is a side elevation view illustrating the first and second tines fully closed;

FIG. 26 is a side elevation view illustrating the clinch in its distal-most position with end portions of the first and second tines extending distally of a shoulder of the applier;

FIG. 27 is a side elevation view illustrating proximal movement of the carriage where the end portions of the clinch engage the shoulder to lock the clinch in its closed position;

FIG. 28 is a perspective view of a multiple-clinch embodiment of the clinch applier;

FIG. 29 is a perspective view of a jaw assembly associated with the applier of FIG. 28;

FIG. 30–FIG. 34 are progressive views illustrating operation of the clinch applier of FIG. 28;

FIG. 30 illustrates a suture surrounding a body conduit and tensioned by a single hand of the surgeon, with a clip applier ready for operative disposition relative to the suture;

FIG. 31 is a perspective view illustrating the clinch applier and a clinch engaging the suture ends;

FIG. 32 illustrates the suture appropriately tensioned with the clinch partially closed to capture the suture ends in a non-fixed relationship;

FIG. 33 is a perspective view illustrating the clinch applier moving the clinch into an operative position with the suture appropriately tensioned to occlude the body conduit;

FIG. 34 is a perspective view showing the clinch applier released from the clinch and the clinch fixed to maintain the tension on the suture;

FIG. 35 is a perspective view of a further embodiment of the clinch including a central bump, and a pair of lateral window frames;

FIG. 36 is a perspective view of the clinch illustrated in FIG. 35 with one of the window frames folded over the bump;

FIG. 37 is a perspective view of the clinch illustrated in FIG. 35 with both of the window frames folded over the bump;

FIG. 38 is a further embodiment of the clinch similar to that illustrated in FIG. 37 and further comprising an integral locking tab associated with the other window frame;

FIG. 45 is a side-elevation view of the clinch applier being operated to engage the proximal end of the spring clinch with the suture ends;

FIG. 46 is a radial cross-section view taken along lines 46—46 of FIG. 46;

FIG. 47 is a side-elevation view similar to FIG. 44 and illustrating axial movement of the clinch applier to place the spring clinch in its operative position;

FIG. 48 is a side-elevation view illustrating the tortuous path followed by the suture ends through the spring clinch as the applier is operated to expel the clinch in its operative position;

FIG. 51 is a perspective view of a further embodiment of the clinch, which is free of any windows or bumps;

FIG. 52 is a perspective view showing the clinch of FIG. 51 operatively placed to engage suture ends; and FIG. 53 is a perspective view showing the clinch of FIG. 51 with the suture ends engaged and forced to follow a tortuous path.

DESCRIPTION OF PREFERRED EMBODIMENTS AND BEST MODE OF THE INVENTION

Figure 1:
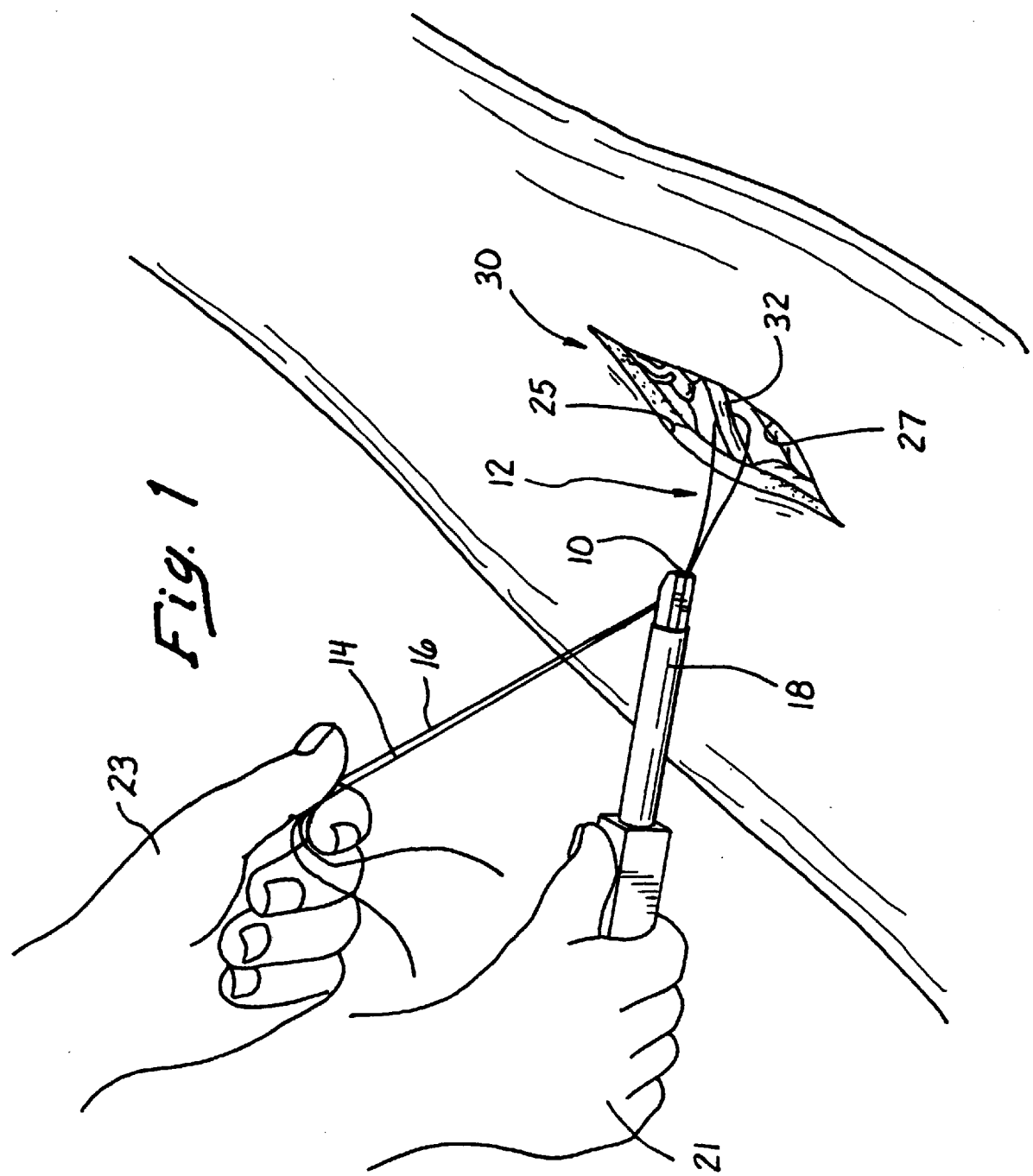
FIG. 1 is a perspective view of a preferred embodiment of a suture clinch and clinch applier operatively positioned for use in a patient.

A suture securing mechanism, hereinafter referred to as a clinch, is illustrated in FIG. 1 and designated by the reference numeral 10. The clinch 10 can be used as an alternative to or in conjunction with a knot for closing and holding in fixed proximity the ends of a suture 12. These suture ends might be the free ends 14 and 16 illustrated in FIG. 1. The clinch 10 would typically be manipulated by an applier 18 preferably operable by one hand 21 of a surgeon. The other hand 23 of the surgeon can be used to place continuous tension on the suture ends 14 and 16. As explained in greater detail below, this is particularly advantageous as the tactile feedback provided by the tensioned suture 12 can aid in attaining the final disposition of the clinch 10.

Figure 2:
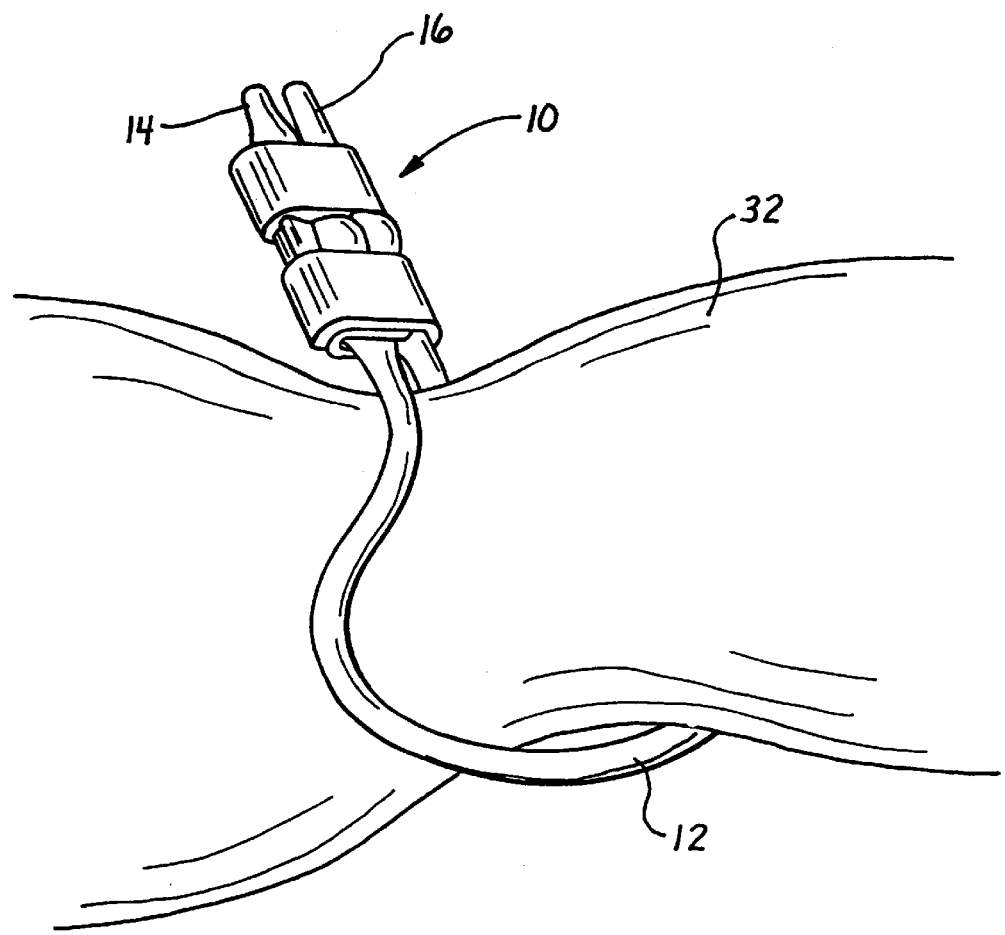
FIG. 2 is an enlarged perspective view of the clinch illustrated in FIG. 1 used in combination with a suture to occlude a body conduit.

The suture 12 can be used in any typical manner. For example, the suture 12 can be used to engage opposing sides 25 and 27 of a wound, such as an incision 30, and to draw these opposing sides 25 and 27 into close, healing proximity. Sutures are also used to occlude body conduits such as a vessel 32 as in FIG. 1. When the suture 12 is used to close the incision 30, it would typically be threaded through the opposing sides 25 and 27. When used for occlusion, the suture 12 would typically be wrapped around the vessel 32 as illustrated in FIG. 2. In either case, it is desirable to bring the suture ends 14 and 16 into a fixed relationship, with tension applied to the suture 12.

Figure 3:
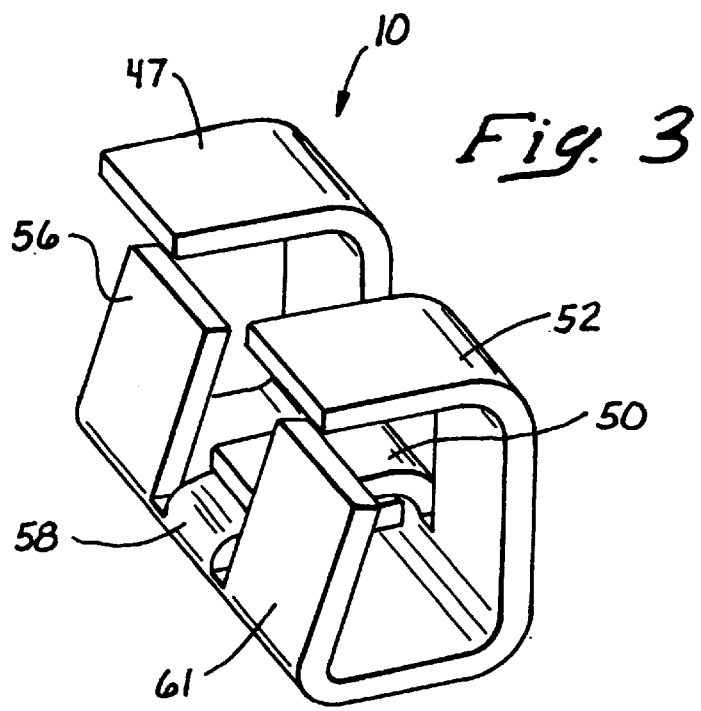
FIG. 3 is a perspective view of the suture clinch in an open state.
Figure 4:
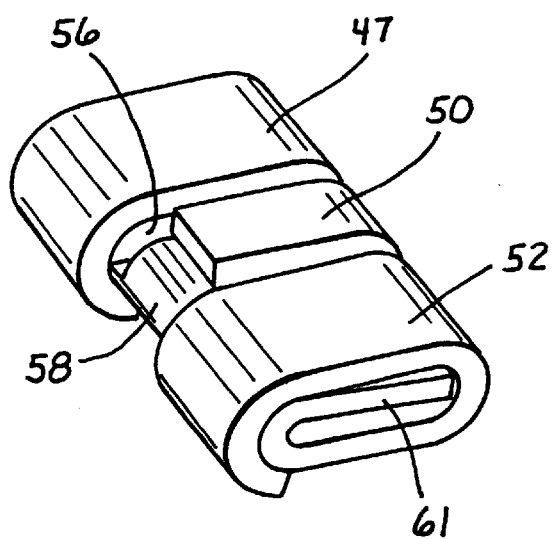
FIG. 4 is a perspective view of the suture clinch in a closed state.

A preferred embodiment of the clinch 10 is shown in greater detail in FIG. 2 where the suture 12 is illustrated to surround the vessel 32, and the clinch 10 is shown in a final position where it maintains the suture ends 14, 16 in a fixed relationship. The clinch 10 can be formed of any suitable metal or non-metal material, or combination thereof. A plastic material with bio-absorbable properties may be of particular interest. In the illustrated embodiment, however, the clinch 10 is formed from metal and is bendable or malleable to accommodate movement between an open position illustrated in FIG. 3, and a closed position illustrated in FIG. 4. In the open position, the clinch 10 is sufficiently open to receive the suture ends 14, 16; in the closed position, the suture ends 14, 16 are held in fixed close proximity to maintain tension on the suture 12.

Figure 5:
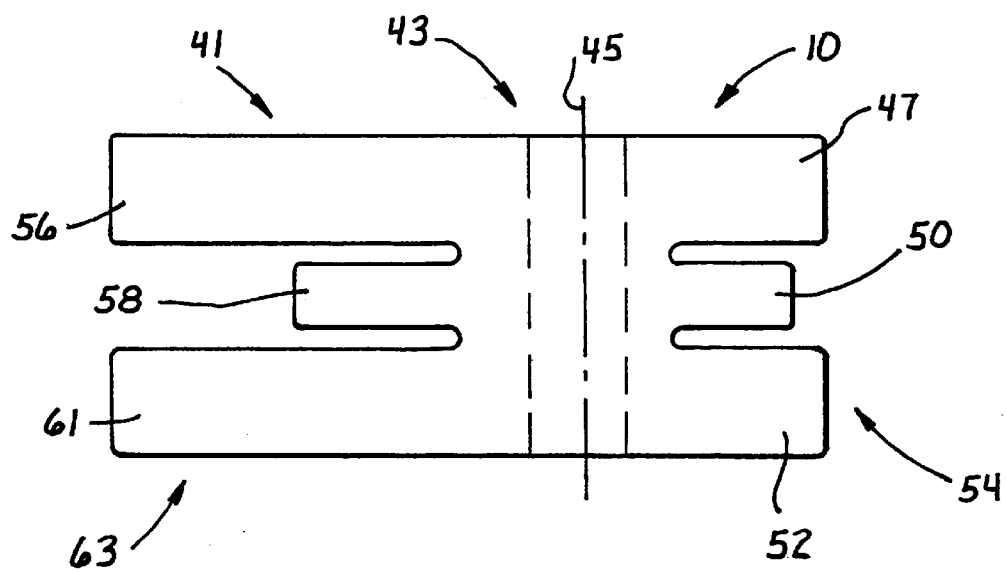
FIG. 5 is a top plan view of a suture clinch showing a preferred layout for stamping the clinch from a sheet material.
Figure 6:
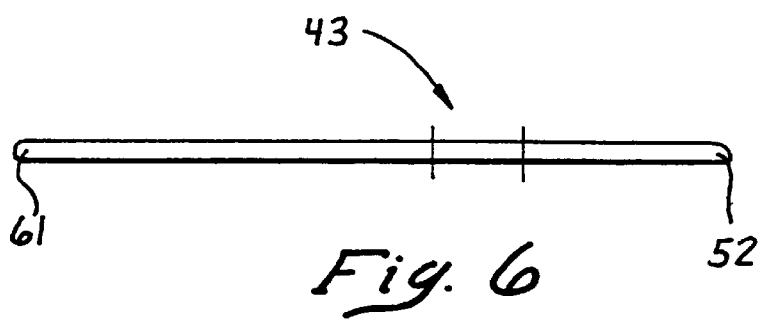
FIG. 6 is a side elevation view of the clinch in the open state.

The clinch 10 can be stamped or otherwise formed from sheet metal 41, as illustrated in FIGS. 5 and 6. In this particular pattern of the clinch 10, an elongate support 43 is provided to extend along an axis 45. On one side of the axis 45, a plurality of tines 47, 50, and 52 are arranged in a first set of tines 54. On the other side of the axis 45, tines 56, 58, and 61 form a second set of tines 63. In this embodiment, each of the tines 47, 50, 52, 56, 58, and 61 extends generally perpendicular to the axis 45, although any transverse relationship between the tines and the axis 45 might be appropriate.

It will also be noted in this embodiment, that each of the tines 47, 50, and 52 in the first set 54 has an associated tine 56, 58, and 61 in the second set 63. These associated pairs of tines, such as the tines 47 and 56, the tines 50 and 58, and the tines 52 and 61, are disposed generally in an opposing relationship. It will be appreciated that other embodiments of the clinch 10 may include a different number of tines, a different number of tines in a particular set, as well as a different length and thickness for the individual tines.

With respect to the clinch 10, illustrated in FIG. 5, an open position is shown in greater detail in the end, back, front, and top views of FIGS. 7–10, respectively. In this open position, one of the first set of tines 54, such as the tine 50, is folded over the support 43 and across the axis 45. The opposing tine in the second set 63, such as the tine 58, is folded over the support 43 and the tine 50 to form a bump 65, best illustrated in FIG. 7. The tines 47 and 52 in the first set 54 are bent to extend generally perpendicular to the plane of the support 43, upwardly in FIG. 7. In this position, the tines 47 and 52 extend above the tines 50 and 58 which form the bump 65 generally centrally between the tines 47 and 52.

Figure 7:
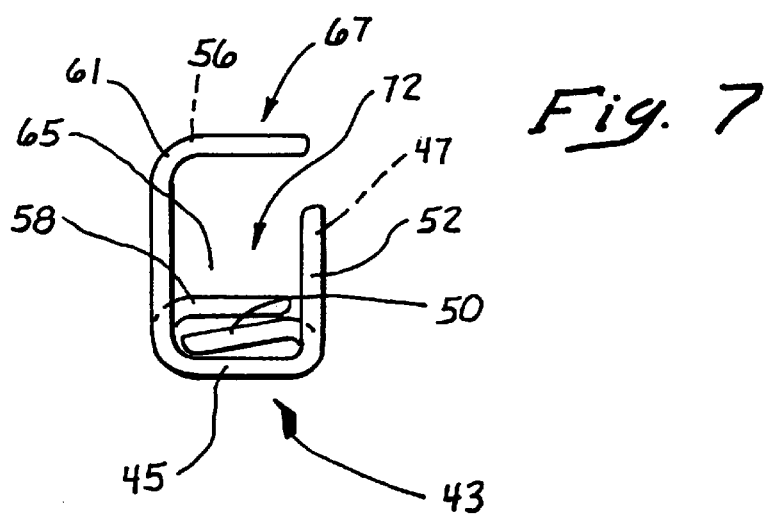
FIG. 7 is an end view of the clinch in the open state.
Figure 8:
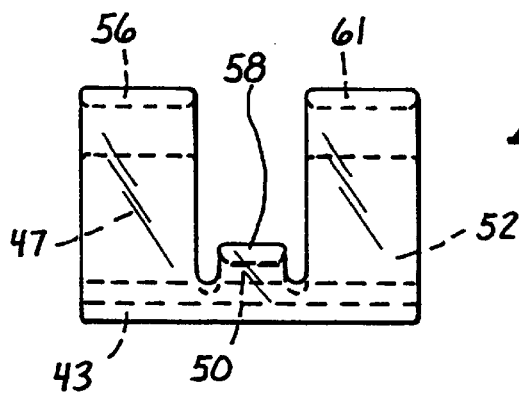
FIG. 8 is a back elevation view of the clinch in the open state.
Figure 9:
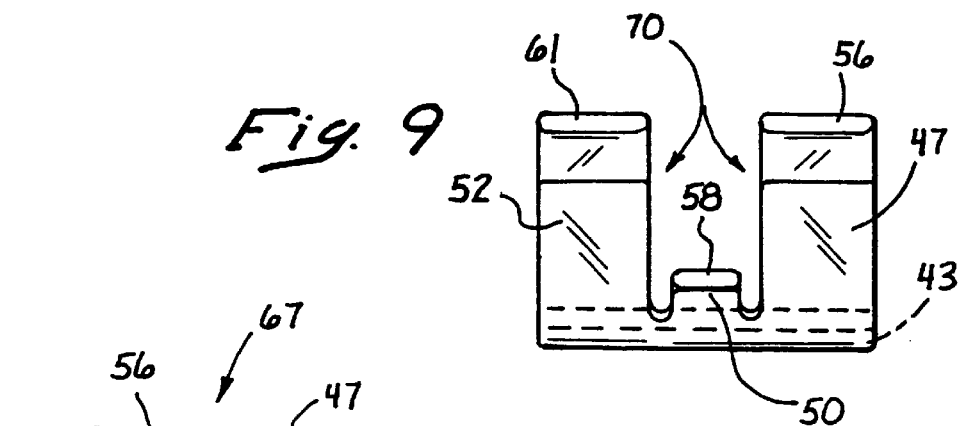
FIG. 9 is a front elevation view of the clinch in the open state.
Figure 10:
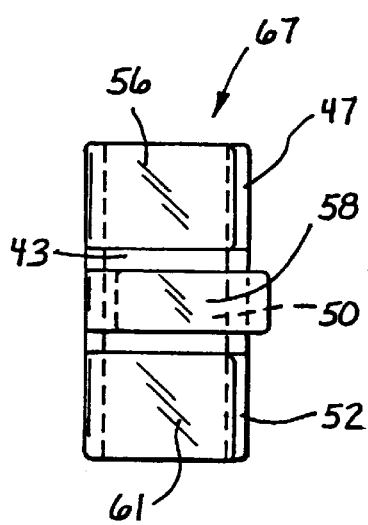
FIG. 10 is a top plan view of the clinch in the open state.

The tines 56 and 61 opposing the tines 47 and 52, respectively, can also be bent to extend generally perpendicular to the support 43, upwardly in FIG. 7. These tines 56 and 61 are relatively long and, therefore, extend above the tines 47 and 52. End portions 67 of the tines 56 and 61 can be bent to extend across the axis 45, over the support 43 and the tines 50, 58, and above the tines 47 and 52. In this open configuration, a space 70 is formed between the ends of the opposing tines 52, 61 and the opposing tines 47, 56. This space 70 is best illustrated in FIG. 9. In this open position, the space 70 is sufficiently large to receive the suture ends 14, 16 into a channel 72 which is defined on the bottom by the bump 65, on the opposing sides by the tines 56, 61, and 47, 52, and on the top by the end portions 67 of the tines 56, 61.

Figure 11:
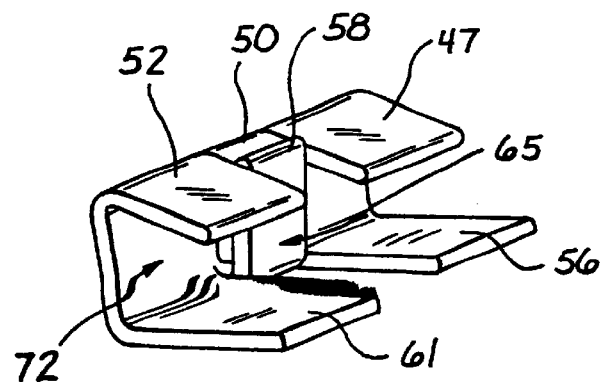
FIG. 11–FIG. 19 illustrate progressive views of the suture clinch disposed with respect to a pair of suture ends and operation in progressive steps between the open state and the closed state.
Figure 12:
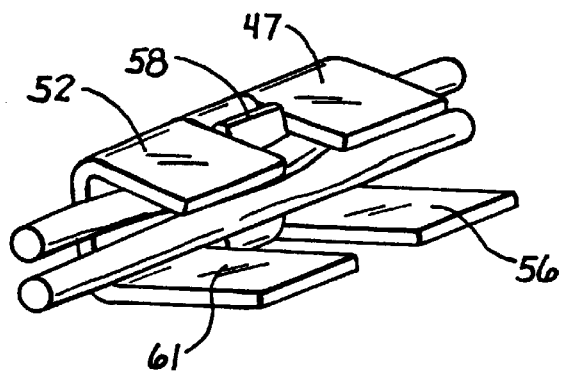
Figure 13:
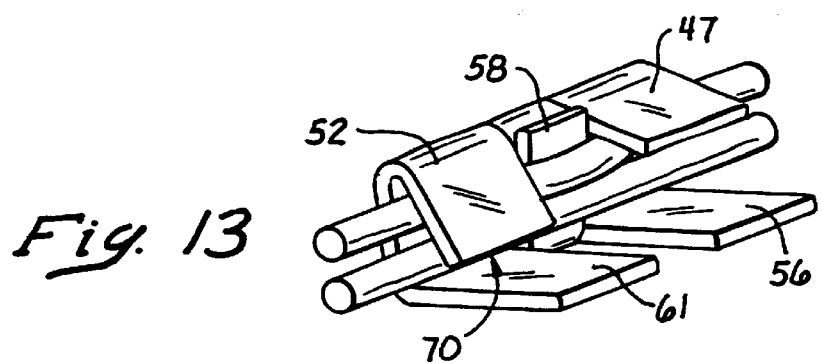
Figure 14:
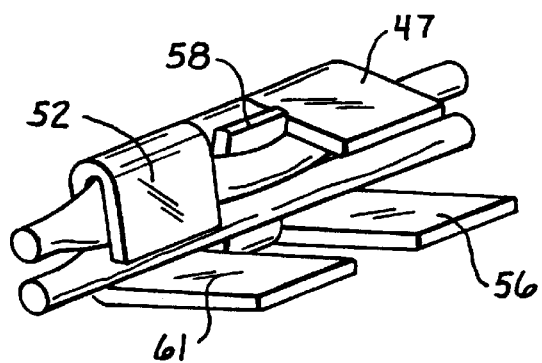
Figure 15:
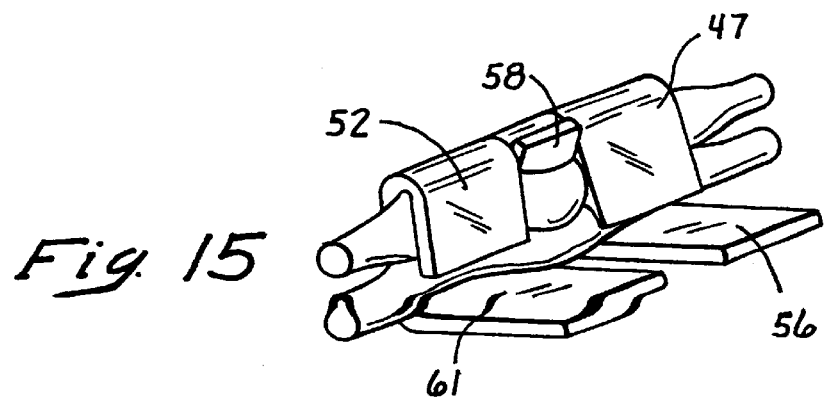
Figure 16:
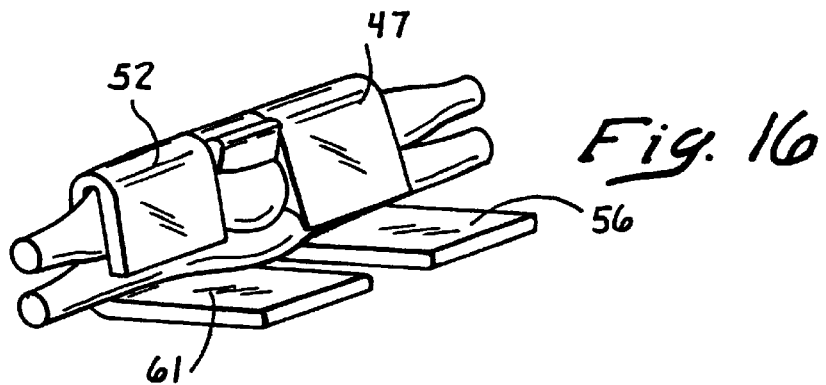
Figure 17:
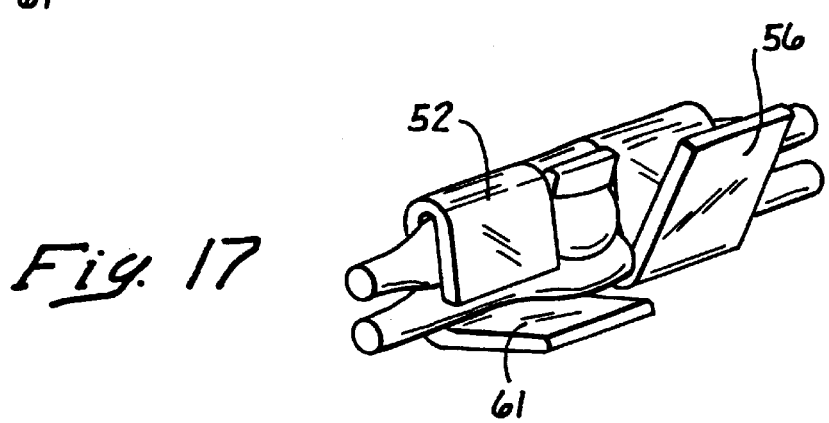
Figure 18:
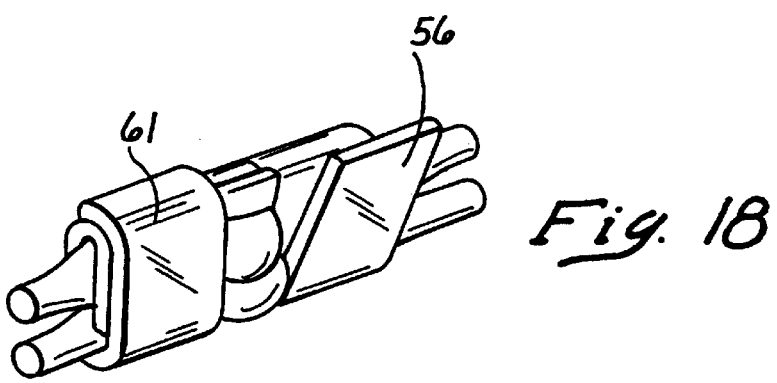
Figure 19:
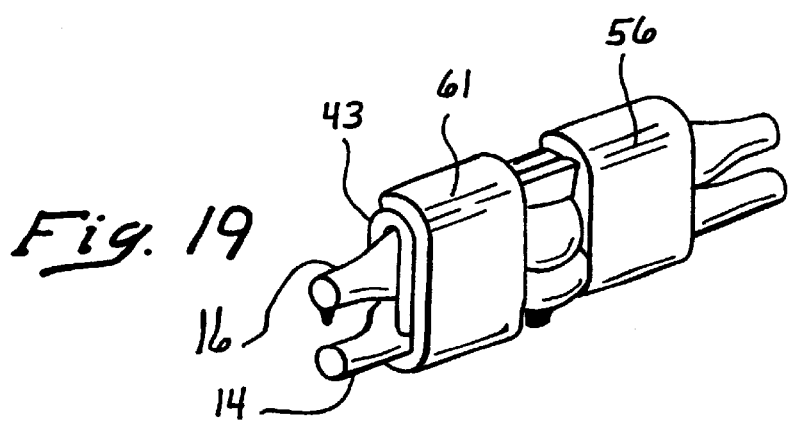

Further manipulation of this preferred embodiment of the clinch 10 can be appreciated with reference to FIGS. 11–19. For example, as illustrated in FIG. 11, the bump 65 can initially be formed in the central region of the clinch 10. Note that during this forming step the height of the bump 65 above the support 43 can be varied by including either one or two of the tines 50, 58. A relatively high bump 65 formed by two of the tines 50, 58 creates a more tortuous path for the suture ends 14, 16, and thereby facilitates traction in the alternate closed or fixed state. When the clinch 10 is in the open state as illustrated in FIG. 11, the suture ends 14, 16 can be placed within the channel 72 which is formed over the support 43 and the bump 65, and between the opposing tines 52, 61 and 47, 56. This preferred placement of the suture ends 14, 16 is illustrated in FIG. 12.

At this point in the process for using the clinch 10, some of the tines 47, 52, 56, and 61 can be bent or otherwise folded generally over the suture ends 14, 16 to reduce the size of the channel 72 and the space 70 between the opposing tines. This manipulation of the clinch 10 captures the suture ends 14, 16 without finally engaging them in a fixed relationship. In this interim state illustrated generally in FIGS. 13–15, the clinch 10 can be slid along the suture ends 14, 16 from a proximate position where the suture ends 14, 16 are loaded, as illustrated in FIG. 12, to a final position where the suture ends 14, 16 are finally fixed with an appropriate tension on the suture 12. Importantly, the clinch 10 in this slideable state can be adjusted at the final position to achieve the best orientation for the suture ends 14 and 16 and the clinch 10.

When the final orientation is achieved, the clinch can be bent or otherwise manipulated to its final, closed state wherein the suture ends 14, 16 are firmly engaged and fixed with an appropriate tension. The steps to this final state are illustrated in FIGS. 16–19 where the tines 56 and 61 are folded over the opposing tines 47 and 52, respectively. Providing these tines 56 and 61 with sufficient length to extend around the side of the support 43 will aid in maintaining this final, fixed state best illustrated in FIG. 19.

Figure 20:
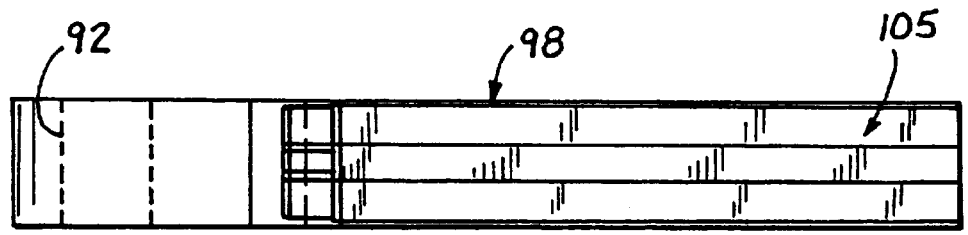
Figure 21:
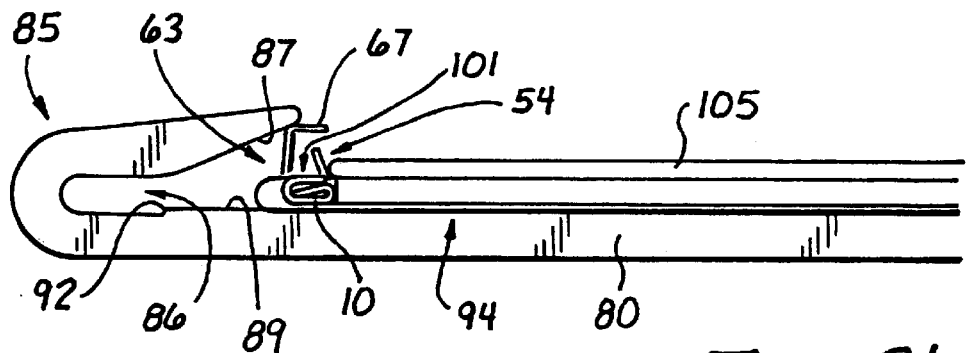

One embodiment of the clinch applier 18 is illustrated in the top and side views of FIGS. 20 and 21, respectively. This applier has a shaft 80 and a proximal end 81 which will typically be held by the hand 21 (FIG. 1) of the surgeon. An opposing distal end 83 is bent back on itself to form a hook 85 which defines a hook channel designated generally by the reference numeral 86. In this embodiment, the hook 85 includes a camming or inclined surface 87 which extends outwardly with progressive proximal positions. The hook 85 also has an inner surface 89 which faces the surface 87 and forms a distally-facing shoulder 92.

The clinch applier 18 includes a carriage 94 which is movable longitudinally along the shaft 80 and is adapted to carry or otherwise move the clinch 10 into the hook channel 86. The carriage 94 in this embodiment includes a distal section 96 and a proximal section 98 which define a slot 101 which is sized and configured to receive the clinch 10. In this case, the clinch 10 is positioned within the slot 101 with its axis 45 extending transverse to the length of the shaft 80. As illustrated in FIG. 21, the clinch 10 is oriented with the second set of tines 63 positioned distally of the first set of tines 54. With this preferred orientation, the end portions 67 of the tines 56 and 61 extend proximally, to the right in FIG. 21.

The proximal section 98 of the carriage 94 may be movable relative to the distal section 96 in order to vary the size of the slot 101. This might be of advantage in an embodiment adapted for different sizes of the clinch 10. Alternatively, the relative movement between the proximal section 98 and the distal section 96 could be used to load the clinch 10 by moving it into engagement with the distal section 96. In a preferred embodiment, the distal and proximal sections 96 and 98, respectively, are maintained in a generally-fixed relationship once the clinch 10 is held within the slot 101.

In the illustrated embodiment, a crimping element 105 is slideable longitudinally along the proximal section 98 of the carriage 94. The distal end of the crimping element 105 includes a pair of lateral projections 107 and 110 which define a central slot 112. This configuration is illustrated in the top view of FIG. 22a. The distal end of the proximal section 98 can be provided with a complimentary configuration including a central projection 114 which defines lateral slots 116 and 118.

Figure 22:
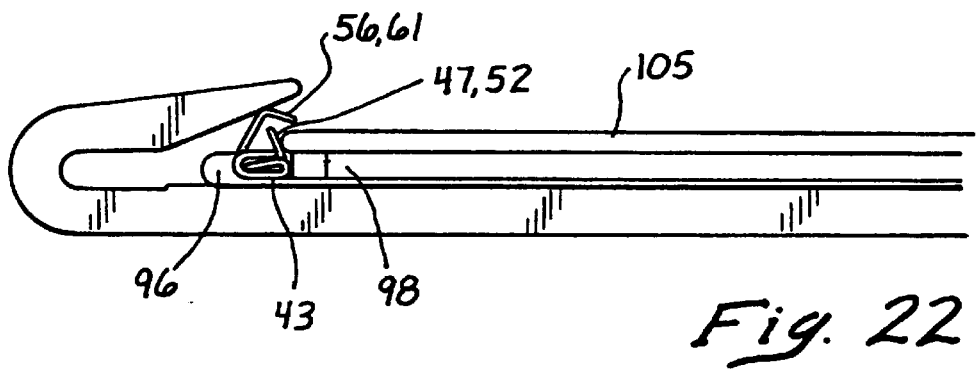
Figure 22A:
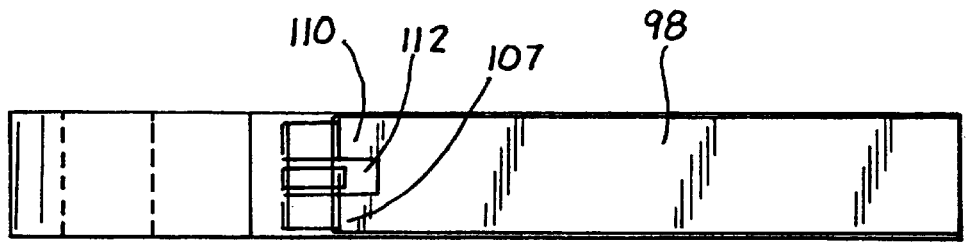
FIG. 22A is a top plan view of a distal end of a clinch actuator associated with applier.

In operation, the clinch-loaded carriage 94 is moved distally until the second set of tines 63 is brought into contact with the camming or inclined surface 87 of the hook 85. Further distal movement causes the outer tines 56 and 61 to be partially bent over the support 43 of the clinch 10. As illustrated in FIG. 22, this aids in firmly holding the clinch 10 within the slot 101 and also seeks to capture the free ends of the suture 12 (FIG. 2).

Figure 23:
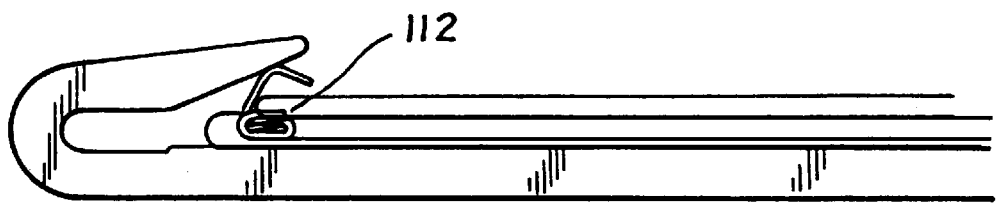

The next step in the method of operation might be to move the crimping element 105 distally. During this movement, the outer tines 47 and 52 in the first set 54 are engaged and bent distally over the support 43 as illustrated in FIG. 23. With this movement, the slot 112 in the crimping element 105 provides space into which the higher bump 65 can pass without interference.

At this point in the process, the suture ends 14, 16 (not shown in FIG. 23) are positioned over the central tines 50 and 58 which define the bump 65. The ends 14 and 16 are captured between the support 43 and the end tines 47 and 52 on either side of the bump 65. Thus, the suture ends 14, 16 are held in a generally fixed relationship in a highly circuitous path.

Figure 22B:
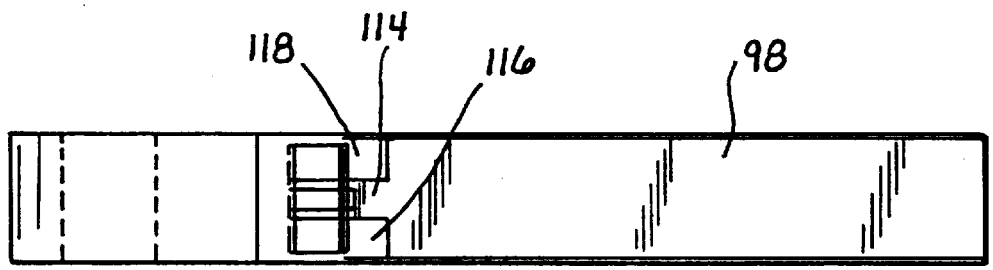
FIG. 22B is a top plan view of the distal end of a proximal element of the clinch carriage associated with the applier.
Figure 24:
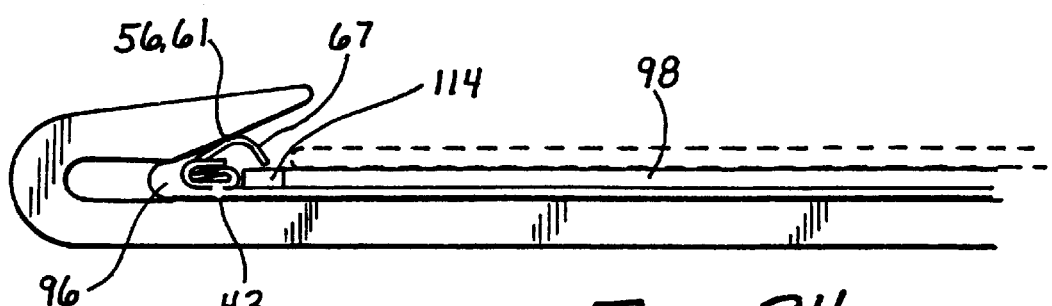
Figure 25:
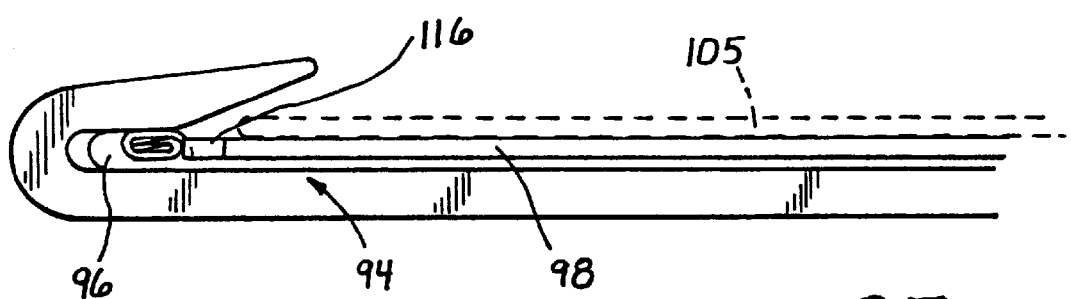

This fixed relationship is further enhanced by moving the tines 56 and 61 downwardly into their final position. This is accomplished in the preferred embodiment by moving the carriage 94 and the clip 10 further into the hook channel 86. During this movement, the tines 52 and 61 are bent downwardly by the inclined surface 87 as shown in FIG. 24. Further movement of the clinch 10 into the hook slot channel 86 will place it in the fully closed configuration best illustrated in FIG. 25. It will be noted that as the tines 52 and 61 are bent downwardly by proximal movement of the carriage 94, they fall into the slots 116 and 118 (FIG. 22b) so that the end portion 67 of these tines 52, 61 can be moved downwardly beyond the support 43 as illustrated in FIG. 25. Further distal movement of the carriage 94 and clinch 10 will cause these end portions 67 to clear the shoulder 92 in the distal section 96 of the carriage 94. From this position, illustrated in FIG. 26, the carriage 94 and clinch 10 can be drawn proximally as shown in FIG. 27. This will cause the tips of the end portion 67 of the tines 52, 61 to be engaged by the shoulder 92 and folded around the edge of the clinch 10 beneath the support 43. In this final state, the suture ends 14, 16 (FIG. 2) will follow a circuitous path which passes over the central tines 50, 58 defining the bump 65, and beneath the opposing lateral tines 47, 56 and 52, 61 on either side of the bump 65.

A further embodiment of a clinch applier is illustrated in FIG. 28 and designated by the reference numeral 121. In this case, the applier 121 includes a housing 123 having an integral palm grip 125 and a finger actuator 127. The housing 123 is longitudinally drilled to form a cylindrical channel 129 which is sized and configured to receive a tube 130 having a hollow working channel 132. A jaw assembly 134, separately illustrated in FIG. 29, is adapted for disposition within the working channel 132 of the tube 130. In the illustrated embodiment, the tube 130 is fixed to the housing 123 and the jaw assembly 134 is movable relative to the housing 123 and the tube 130 by operation of the finger actuator 127.

The jaw assembly includes a pair of jaws 136 and 138 which are configured to receive the clinch 10 and to fix the clinch 10 around the suture ends 14, 16 (FIG. 2). In the illustrated embodiment, the lower jaw 137 extends into a longitudinal shaft 139. A groove 141 is formed longitudinally in the shaft 131 and sized to receive a plurality of the clinches 10 for collective movement along the shaft 139 and individual movement into the jaws 135 and 137. The groove 141 in the shaft 139 extends into a transverse groove 143 which is formed in the lower jaw 137. As the clips 10 are moved along the axial groove 141, they are individually pushed into the transverse groove 143 for manipulation by the jaws 135 and 137. The axial orientation of the groove 141 is preferred in order to facilitate movement of the clinches 10 along the shaft 141. The transverse orientation of the groove 143 is preferred in order to facilitate engagement of the suture ends 14, 16.

After one of the clinches 10 has been moved between the jaws 135 and 137, the ends 14, 16 of the suture 12 can be positioned within the groove 143 and the clinch 10. The jaws 135 and 137 can then be drawn into proximity by moving the jaw assembly 134 relative to the tube 130. This relative movement can be achieved by fixing the tube 130 to the housing 123, as previously discussed, or by fixing the jaw assembly 134 with respect to the housing 123 and moving the tube 130 by operation of the finger actuator 127.

Figure 30:
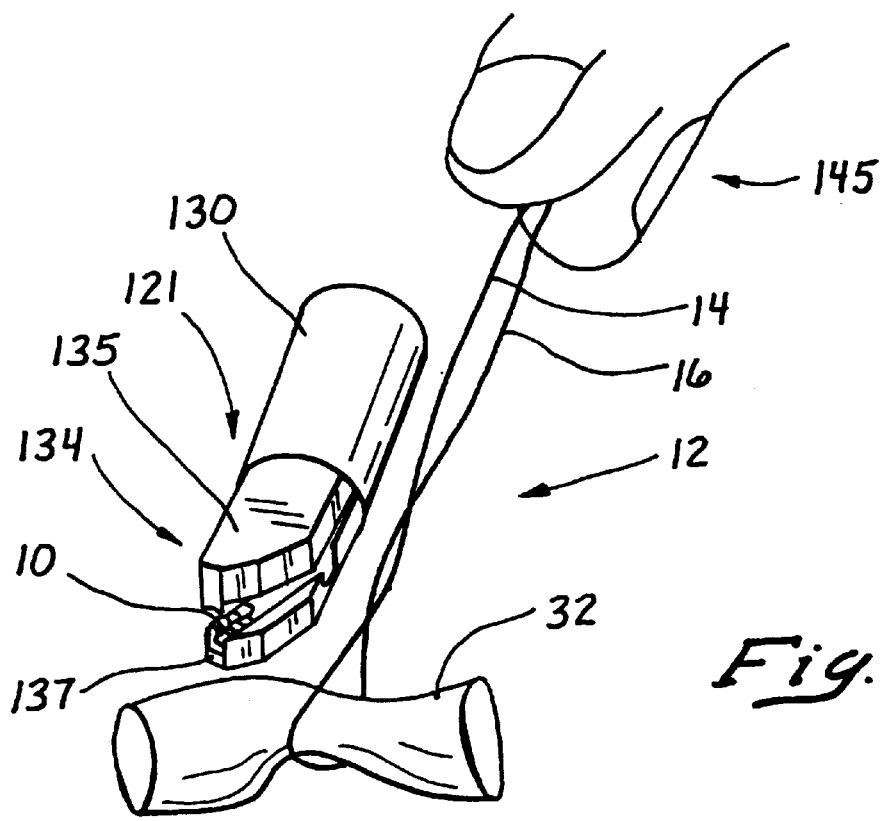
Figure 31:
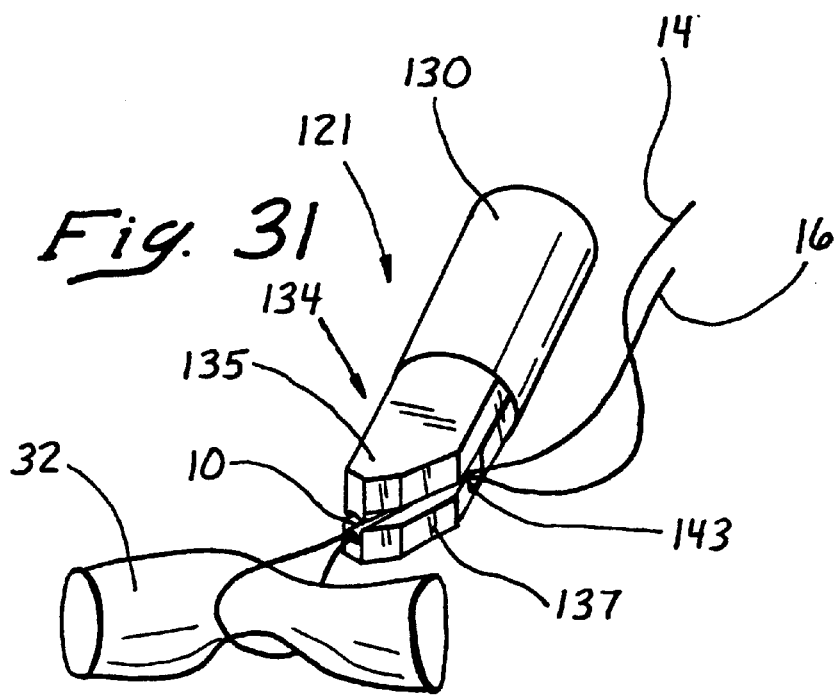
Figure 39:
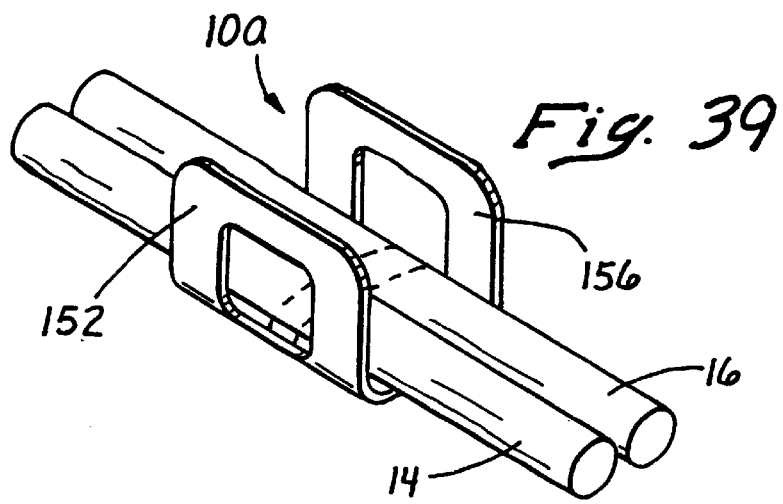
FIG. 39 is a perspective view of the clinch illustrated in FIG. 35 with a pair of suture ends disposed within the clinch.
Figure 40:
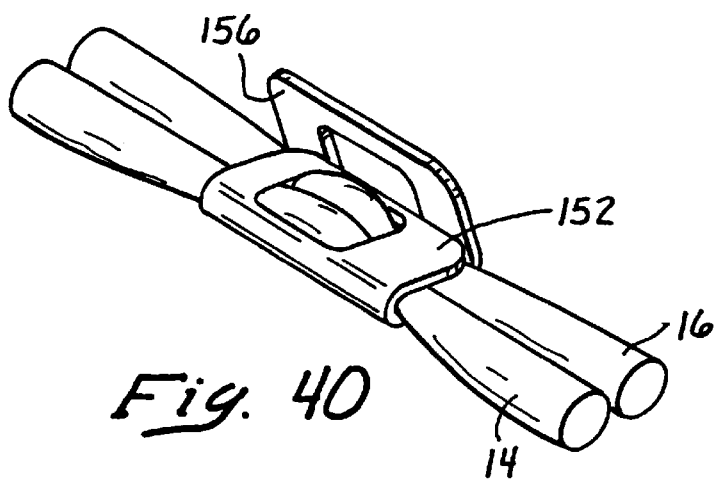
FIG. 40 is a perspective view of the clinch illustrated in FIG. 39 with one of the window frames folded over the suture ends.
Figure 41:
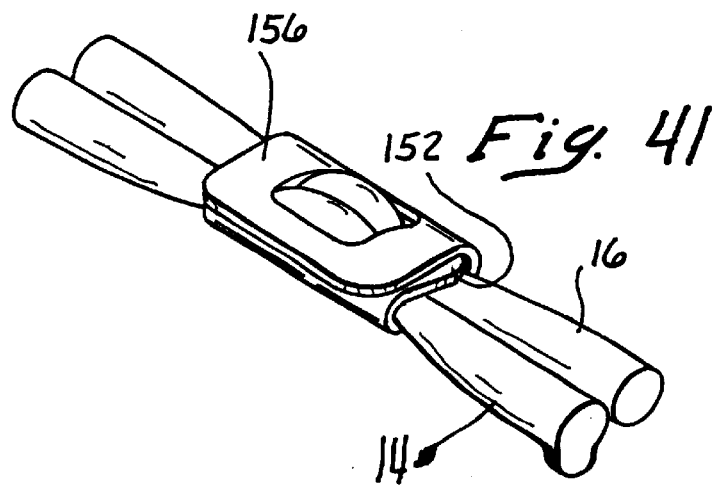
FIG. 41 is a perspective view of the clinch illustrated in FIG. 39 with both of the window frames folded over the suture ends.

Operation of the clinch applier 121 can be better understood with reference to FIGS. 30–34. In FIG. 30, the suture 12 is illustrated to be looped around the vessel 32 with tension applied to the suture ends 14, 16 by fingers 145 of the surgeon. The clinch applier 121 can then be moved into proximity with the suture 12. At this point, it will be noted that the clinch applier 121 is operable by only one hand of the surgeon. This leaves the fingers 145 of the other hand available to tension the suture 12. By thus manipulating both the clinch applier 121 and the suture 12, the ends 14 and 16 can be moved into the transverse groove 143 and into the clinch 10 as illustrated in FIG. 31. It will be appreciated that the transverse orientation of the groove 143 is particularly advantageous in this loading step. With the clinch 10 in its open state, the ends 14 and 16 can be easily disposed within channel 22 (FIG. 7) of the clinch 10.

At this point, the clinch applier 121 can be operated to partially close the clinch 10, as illustrated in FIG. 32. This partial closure is achieved by moving the jaws 135 and 137 into proximity so that the suture ends 14, 16 loosely captured within the clinch 10. In this condition, the suture ends 14 and 16 are generally enclosed by the tines of the clinch 10, but not rigidly fixed to the clinch 10. This interim state of the clinch 10 offers significant advantages in loosely capturing the suture ends 14, 16 while at the same time permitting movement of the clinch 10 along the suture 12 to its final position as illustrated in FIG. 33. Note that during this moving step, the fingers 145 of the surgeon can maintain tension on the suture 12 with the other hand of the surgeon moving the clinch applier 121 and the clinch 10 to its final position.

Once the clinch 10 is adjusted at its final position, the clinch applier 121 can be further operated to close the jaws 135 and 137. This will cause the tines of the clinch 10 to firmly grip the suture 12 and hold the ends 14 and 16 in a fixed relationship. Having thus applied the clinch 10 to fixedly engage the suture ends 14, 16, the applier 121 can be removed as illustrated in FIG. 34.

It will be noted that in this process, the single-handed manipulation of the clinch applier 121 frees the second hand of the surgeon to maintain tension on the suture 12 throughout the process. This tension greatly facilitates the initial step of placing the suture ends 14 and 16 into the transverse groove 143. It also facilitates the step of adjusting the clinch 10 at its final location before firmly gripping the suture ends 14 and 16. During this adjustment process, tension on the suture 12 is translated directly to the suture site so that final crimping of the clinch 10 maintains the desired tension on the tissue, such as the vessel 32.

Having disclosed preferred embodiments of both the clinch 10 and associated clinch appliers, such as the applier 121, it will now be apparent that the clinch can be embodied in many different forms, each providing some advantage over traditional forms of knot tying. Clinch appliers, preferably operable to engage sutures laterally along their length, can be operated to issue, perhaps move, and perhaps close each clinch embodiment.

Realizing that it is the tortuous path required by the clinch and not necessarily the extreme pressure of the clinch on the sutures which is of particular interest to certain embodiments. Tortuous paths can be created with many different embodiments of the clinch such as that illustrated in FIGS. 35–41. In this embodiment, elements of structure which are similar to those previously discussed will be designated with the same reference numerals followed by the lower-case letter "a". For example, with reference to FIG. 35, the clinch 10a is illustrated to include a support 43a extending along an axis 45a and including a bump 65a. On one side of the support 43a, a frame 152 defines a window 154. Similarly, on the other side of the support 43a, a frame 156 defines a window 158.

Movement of the clinch 10a from an open state to a closed state may occur by operation of an associated clip applier (not shown), or may be inherent within the memory characteristics of the clinch 10a. This movement toward the closed state in this case will typically include folding of the frame 152 over the support 43a. This action preferably brings the window 154 over the bump 65a. A second folding motion includes the frame 166 which can be folded over the support 43a and the window frame 152, as illustrated in FIG. 37. Again, the window 158 is preferably located over the bulge 65a and the window 154. FIG. 38 illustrates a further embodiment wherein the frame 156 includes the portions 67a with a length sufficient to extend around the frame 152 and lock the clinch 10a in its closed position.

Figure 42:
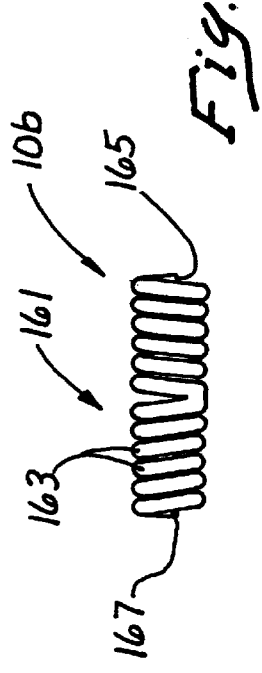
FIG. 42 is a side-elevation view of a spring embodiment of the clinch associated with the present invention.

It is not only advantageous to accentuate the tortuous path over the pressure of the clinch, but also desirable to insure that the clinch does not significantly compress or notch the fragile suture. An embodiment of the clinch which is particularly adapted to avoid sharp corners is that illustrated in FIGS. 42–48 where similar elements of structure are designated by the same reference numeral followed by the lower-case letter "b". In FIG. 42, it can be seen that the clinch 10b can be provided with a configuration of a spring 161 having multiple convolutions 163 wound between a distal end 165 and a proximal end 167. The spring 161 is preferably formed of wire having a cross-section free of sharp corners, such a circular. It will be noted that the convolutions 163 of the spring 161 all can be wound in the same direction, or alternatively, the convolutions 163 can be wound in different directions, as illustrated in FIG. 42.

Figure 43:
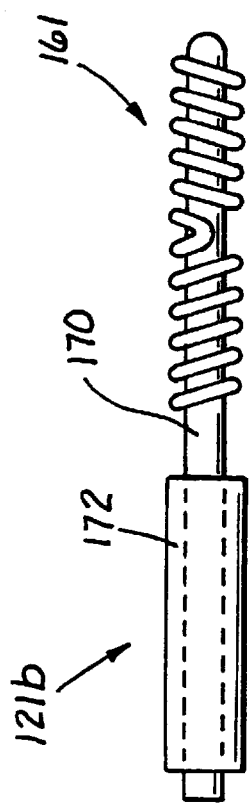
FIG. 43 is a side-elevation view of a spring clinch applier.
Figure 44:
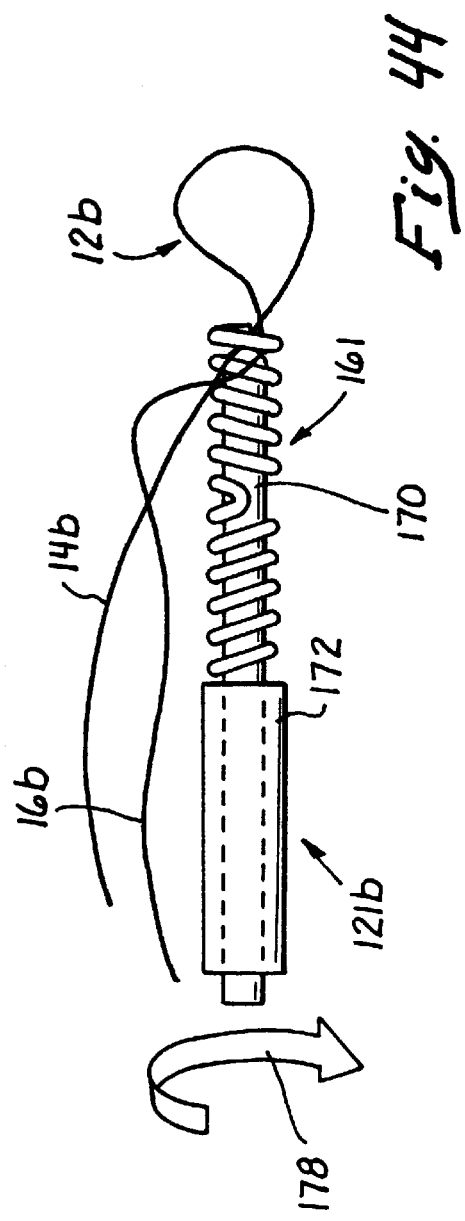
FIG. 44 is a side-elevation view of the clinch applier being operated to engage suture ends with a distal end of the spring clinch.

A suitable applier 121b for the spring-clinch 161 might be that illustrated in FIG. 43 to include a shaft 170 and a coaxial ejecting sleeve 172. In operation, the spring 161 can be tightly mounted on the shaft 170 distally of the ejection sheath 172. With the suture ends 14b and 16b held in one hand, the clinch applier 121b can be moved to engage the suture ends 14b, 16b with the distal end 165 of the spring 176. Turning the clinch applier 121b axially causes the suture ends 14b, 16b to move progressively along convolutions 163. In the illustrated embodiment, the clinch applier 121b is turned counterclockwise, as illustrated by arrow 178. It can be seen that with this rotational movement of the spring 161 with respect to the suture 12b, the suture ends 14b, 16b are automatically drawn into a tortuous path which initially extends axially of the spring 161 and then extends radially of the spring 161.

The tortuous path can be further accentuated by threading the suture ends 14b, 16b onto the proximal end 167 of the spring 161, as illustrated in FIG. 45. Since the proximal end 167 remains on the shaft 170, this threading step can be facilitated by providing the shaft 170 with a flat or groove 183. The flat 183 is perhaps best illustrated in FIG. 46 where the proximal end 167 of the spring 161 is shown to be spaced from the shaft 170 to permit threading of the suture ends 14b, 16b. After the suture ends 14b and 16b have been engaged by the spring 161, the applier 121b can be used to push the spring 161 distally, along arrow 181 in FIG. 47, to its operative position relative to the body conduit.

In FIG. 48, the spring clinch 161 is illustrated after its expulsion from the shaft 170 by the sheath 172 in the direction of an arrow 185. Following this operation, the entire clinch applier 18b can be removed from the operative site, for example, axially along an arrow 187.

Figure 50:
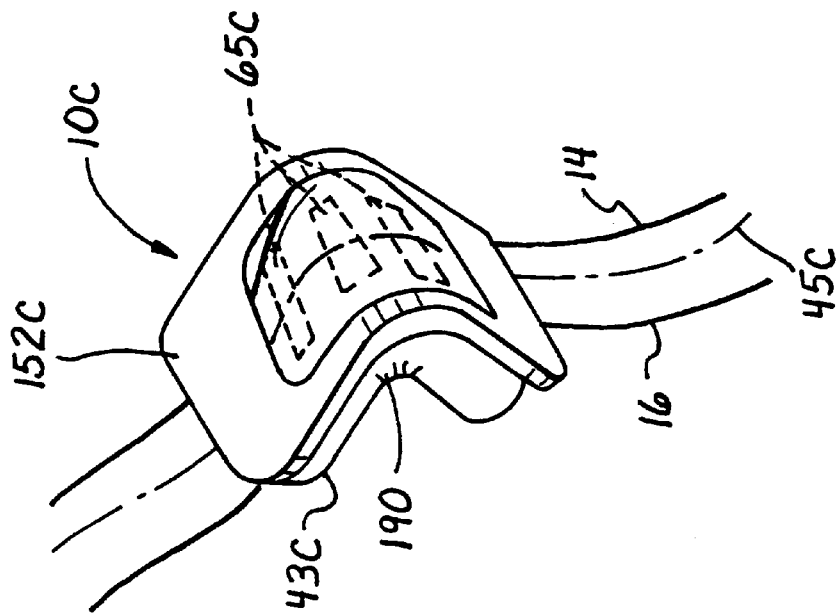
FIG. 50 is a perspective view of the clinch illustrated in FIGS. 9 with the clinch bent along a line transverse to the clinch axis in order to form a tortuous path.
Figure 49:
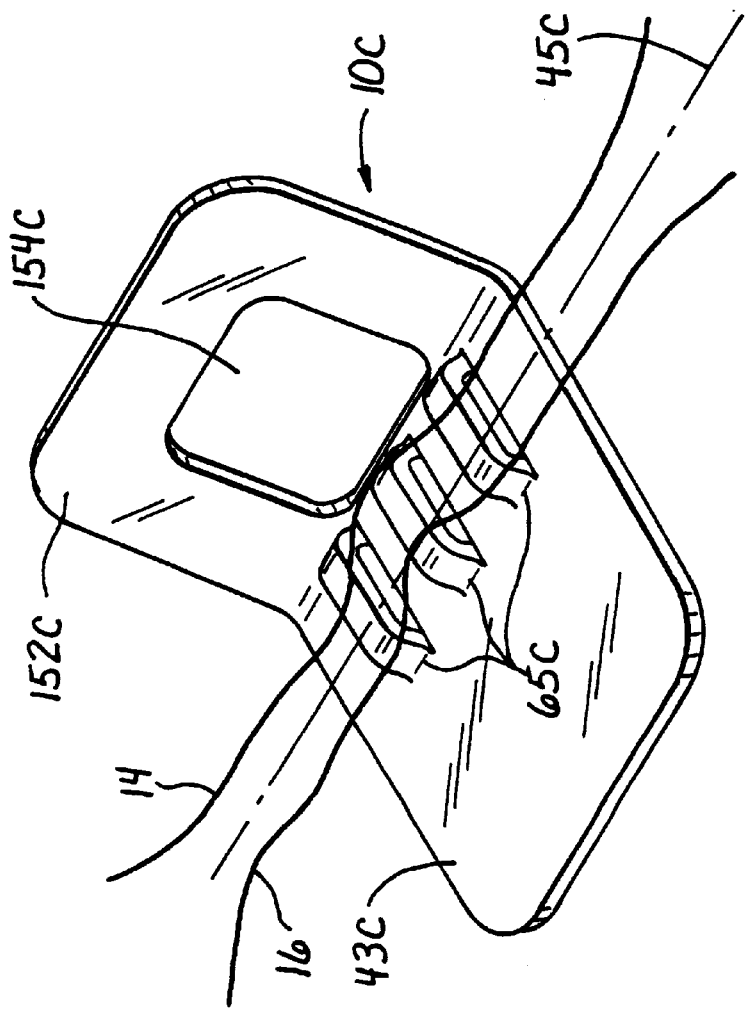
FIG. 49 is a perspective view of a further embodiment showing the clinch in an open state.

A further embodiment of the clinch 10 is illustrated in FIGS. 49 and 50 where elements of like structure are designated by the same reference numeral followed by the lower case letter "c". In this case, the clinch 10c includes a support 43c, which may initially have a generally planar configuration as illustrated in FIG. 49, and which extends along an axis 45c. A single frame 152c is bendable along a side of the support 43c to sandwich the suture ends 14, 16 between the support 43c and the frame 152c. In this embodiment, the clinch 10c is bendable transverse to the axis 45c so that the suture ends 14, 16 are forced to follow a tortuous path through the clinch 10c This tortuous path can be further enhanced by providing a bump 65c in the support 43c, or defining a window 154c in the frame 152c. In the illustrated embodiment, the clinch 10c is bent along a line 190 which is generally perpendicular to the axis 45c.

A further embodiment of the invention, similar to that of FIG. 49, is illustrated in FIGS. 51–53 wherein like elements of structure are designated by the same reference numeral found by the lower-case letter "d." Thus, the clinch 10d includes the central section 43d which extends along the axis 45d. A pair of side panels 192 and 194, which may be integral with the central support 43d, are individually bendable over the center support 43d along dotted lines 196 and 198, respectively.

It will be noted that this embodiment is free of any windows, such as the window 154 (FIG. 5) and any bumps, such as the bumps 65a (FIG. 35). Nevertheless, the clinch 10d is adapted to receive the suture ends 14d, 16d along the axis 45d and to capture the suture ends 14d, 16d by bending the panels 192, 194 over the center support 43d. After the suture ends 14d, 16d are enclosed between the central panel 43d on one side, and the side panels 192, 194 on the other side, the clinch 10d can be bent along the line 90d which is transverse to the axis 45d. This creates the tortuous path which is of particular advantage to the present invention.

This embodiment further emphasizes the desirability of engaging the suture ends 14, 16 and forcing them to individually follow a tortuous path which maintains each of the suture ends 14, 16 in a generally fixed relationship with the clinch 10d. With both of the suture ends 14, 16 fixed to the clinch 10d, they also have a generally fixed relationship with respect to each other. In this respect, the clinch 10 functions as a knot, but the suture end 14, 16 do not experience the sharp bends and high pressures associated with knots and other fixation devices of the past. Although the clinch 10 may apply some pressure to the suture ends 14, 16, it is intended generally that this pressure be sufficiently low that the suture ends 14, 16 are not scored or otherwise weakened in proximity to the clinch 10.

Although certain preferred embodiments of the invention have been discussed, it will be apparent that many of the features and functions of these embodiments can be combined to offer particular advantages under different operative conditions. Certainly, the clinch 10 can be provided with many different configurations each placing the suture ends 14, 16 along a tortuous path to maintain them in a generally fixed relationship. Providing the clinch 10 with characteristics for operation in three stages may be desirable where an interim stage captures the suture without firmly fixing the suture ends. This permits minor adjustments of the clinch 10 at the operative site and further permits the application of desired tension on the suture 12 prior to complete closure.

The clinch 10 can be formed from a variety of materials. One such material might be a preformed spring-hardened material or memory metal which facilitates formation of the final shape of the clinch. Such memory metals might include shape memory alloys such as nickel-titanium which can be formulated to achieve a predetermined shape in response to a particular temperature. A material such as Nitinol would be particularly desirable for this purpose. The super elastic properties of such materials will also be advantageous in that the clinch 10 can be formed in its closed state and then moved to its opened state without fatiguing the material.

In still a further embodiment, the clinch 10 could be formed of a bi-metallic material having properties for taking the desired shape by heating, for example,, using the body temperature. In such a case, the clinch 10 would be supplied in a cold state and then allowed to attain the final shape when heated by the body.

Appliers used with clinches formed from these materials need only issue the clinch and move it to its final position. The applier is not required to change the form of the clinch which will respond to body temperature to achieve its final state. On the other hand, the clinch applier could be provided with a heated tip to facilitate the temperature differential required to change the shape of the clinch.

The various clinches 10 can be operated by a variety of appliers, each preferably adapted for one-hand operation and facilitating the placement and closure of either single or multiple clinches. A variation of the clinch appliers previously discussed, might include a tool which initially receives the clinch in a generally closed configuration, opens the clinch to receive the suture ends 14 and 16, and then closes the clinch or permits closure of the clinch.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

What is claimed is:

1. A suture securing system adapted to move and hold tissue portions in close proximity comprising:

an elongate suture having a pair of ends and being adapted for disposition relative to the tissue portions leaving the suture ends free;

a securing mechanism having a first position for capturing the suture ends, a second position for holding the suture ends along a torturous path and in a fixed relationship with the suture tensioned to maintain the tissue portions in close proximity, and a third position for frictionally engaging the suture ends to hold the suture ends while permitting sliding of the securing mechanism relative to the suture ends; said securing mechanism having a plurality of tines each having an open state and a closed state; and at least one of the tines being in the closed state when the securing mechanism is in the third position.

2. The suture system recited in claim 1 and adapted for operation by a surgeon, wherein:

the securing mechanism is adapted for movement between its first position and second position by engagement of the securing mechanism with only one of the hands of the surgeon.

3. A securing mechanism for securing a pair of free ends of a suture, comprising:

a support having a first side and a second side;

a first set of tines bendable on the support between a first position in juxtaposition to the first side of the support, and a second position overlying the support;

a second set of tines coupled to the support in juxtaposition to the second side of the support;

the securing mechanism having a first state facilitating receipt of the suture ends and a second state facilitating maintenance of the suture ends in a fixed relationship to each other; and at least one of the first set of tines being disposed in the second position when the securing mechanism is in the first state.

4. The securing mechanism recited in claim 3, wherein:

the securing mechanism has a third state facilitating capture of the suture ends while maintaining a sliding relationship with the suture ends; and at least one of the first set of tines and the second set of tines being folded over the support in the third state.

5. The securing mechanism recited in claim 4 wherein each of the tines is in the second position when the securing mechanism is in the second state.

6. The securing mechanism recited in claim 3 wherein at least one of the second set of tines is folded over at least one of the first tines when the securing mechanism is in the second state.

7. The securing mechanism recited in claim 6 wherein each of the second set of tines is disposed in opposing relationship with an associated one of the first set of tines and is folded over the associated first tine in the second position.

8. The securing mechanism recited in claim 3 wherein the support and the tines are formed of metal.

9. The securing mechanism recited in claim 8 wherein the metal is malleable.

10. The securing mechanism recited in claim 8 wherein the support and the tines are integrally formed from sheet metal.

11. The securing mechanism recited in claim 3 wherein the support and the tines are integrally formed from a material having properties for changing shape in response to changes in temperature.

12. The securing mechanism recited in claim 11 wherein the material is spring-hardened.

13. The securing mechanism recited in claim 11 wherein the material includes a memory metal.

14. The securing mechanism recited in claim 11 wherein the material includes a nickel-titanium alloy.

15. A securing mechanism recited in claim 3, wherein:

at least one of the second set of tines is disposed in the second position when the securing mechanism is in the first state.

16. The securing mechanism recited in claim 15, wherein:

all of the tines are disposed in the second position when the securing mechanism is in the second state.

17. A securing mechanism for securing a pair of free ends of the suture, comprising:

a support having a first side and a second side;

a first set of tines extendable in overlying relationship with the support from the first side of the support;

a second set of tines extendable over the support from the second side of the support;

a first one of the first set of tines and a first one of the second set of tines forming a first tine pair;

a second one of the first set of tines and a second one of the second set of tines forming a second tine pair in juxtaposition to the first tine pair;

a pair of suture ends having a first side and an opposing second side; and the first tine pair being in contact with the first side of the suture ends and the second tine pair being in contact with the second side of the suture ends to hold the suture ends in a fixed relationship between the first tine pair and the second tine pair.

18. The securing mechanism recited in claim 17 wherein the pair of suture ends are held in the fixed relationship between the support and the first tine pair.

19. A method for fixing a tensioned suture having a pair of free ends, comprising the steps of:

providing a suture-securing mechanism with a support and a plurality of tine pairs, each having two tines bendable in opposing directions to overlap the support;

bending a first tine pair to overlap the support;

placing the suture ends over the support and the first tine pair;

bending a second tine pair to overlap the suture ends and the support;

frictionally engaging the suture ends between the first tine pair and the second tine pair; and frictionally engaging the suture ends between the second tine pair and the support.

20. A method for fixing a tensioned suture having a pair of free ends, comprising the steps of:

providing a suture mechanism having a first position wherein the mechanism is adapted to receive the suture ends, and a second position wherein the mechanism is adapted to hold the suture ends in a fixed relationship the suture mechanism being bendable to move between the first position and the second position;

receiving the free ends of the suture in the securing mechanism when the securing mechanism is in the first position; and moving the securing mechanism to the second position with the suture ends disposed in the securing mechanism, the suture ends following a tortuous path through the securing mechanism in the second position to maintain the securing mechanism in a fixed position along the suture ends and to maintain the suture ends in a fixed relationship within the securing mechanism.

21. The method recited in claim 20 adapted to be performed by a surgeon, further comprising the steps of:

during the receiving step placing tension on the suture ends using only one of the hands of the surgeon; and during the moving step maintaining the tension on the suture ends using the one hand of the surgeon while moving the securing mechanism using the other of the hands of the surgeon.

22. The method recited in claim 20 wherein the providing step includes the step of forming the securing mechanism from sheet metal.

23. The method recited in claim 22 wherein the providing step further comprises the step of:

providing the securing mechanism with characteristics including a third position wherein the suture ends are captured by the securing mechanism in slideable engagement with the securing mechanism.

24. The method recited in claim 23 further comprising the steps of:
  placing the securing mechanism in the third position after the receiving step; and
  sliding the securing mechanism along the suture ends to a final position while maintaining tension on the suture ends in response to tactile feedback.

25. The method recited in claim 24 wherein the sliding step includes the step of:
  adjusting the securing mechanism along the suture ends at the final position.

26. The method recited in claim 20 wherein the providing step includes the step of forming the securing mechanism from a malleable metal.

27. The method recited in claim 20 further comprising the step of knotting the suture ends prior to the receiving step.

* * * * *